(12) United States Patent
Schwartz et al.

(10) Patent No.: US 10,335,449 B2
(45) Date of Patent: Jul. 2, 2019

(54) RHO ASSOCIATED KINASE (ROCK) INHIBITORS AND THEIR USE IN TREATING DISEASE

(71) Applicant: UNIVERSITY OF HOUSTON SYSTEM, Houston, TX (US)

(72) Inventors: Robert J. Schwartz, Houston, TX (US); Hua Zhang, Houston, TX (US); John W. Craft, Houston, TX (US); Scott Gilbertson, Houston, TX (US); Kevin MacKenzie, Houston, TX (US); Reza Abbasgholizadeh, Houston, TX (US); Steven Bark, Houston, TX (US); James M. Briggs, Houston, TX (US); Robert Fox, Galveston, TX (US)

(73) Assignee: University of Houston System, Houston, TX (US)

( * ) Notice: Subject to any disclaimer, the term of this patent is extended or adjusted under 35 U.S.C. 154(b) by 0 days.

(21) Appl. No.: 15/516,833

(22) PCT Filed: Oct. 1, 2015

(86) PCT No.: PCT/US2015/053503
§ 371 (c)(1),
(2) Date: Apr. 4, 2017

(87) PCT Pub. No.: WO2016/057306
PCT Pub. Date: Apr. 14, 2016

(65) Prior Publication Data
US 2017/0296617 A1  Oct. 19, 2017

Related U.S. Application Data

(60) Provisional application No. 62/060,336, filed on Oct. 6, 2014.

(51) Int. Cl.
| A61K 38/07 | (2006.01) |
| C07K 14/47 | (2006.01) |
| A61K 38/00 | (2006.01) |
| C07K 5/107 | (2006.01) |
| A61K 38/08 | (2019.01) |
| A61K 38/10 | (2006.01) |
| A61K 45/06 | (2006.01) |

(52) U.S. Cl.
CPC ............ *A61K 38/07* (2013.01); *A61K 38/005* (2013.01); *A61K 38/08* (2013.01); *A61K 38/10* (2013.01); *A61K 45/06* (2013.01); *C07K 5/1016* (2013.01); *C07K 14/4703* (2013.01)

(58) Field of Classification Search
None
See application file for complete search history.

(56) References Cited

U.S. PATENT DOCUMENTS

| 8,476,295 B2 | 7/2013 | Lampe et al. |
| 2005/0100965 A1* | 5/2005 | Ghayur ............... C07K 16/244 435/7.1 |
| 2006/0034853 A1 | 2/2006 | Yuen et al. |
| 2008/0057063 A1 | 3/2008 | Rinkenberger et al. |
| 2011/0296543 A1 | 12/2011 | Chang et al. |
| 2013/0059839 A1 | 3/2013 | Lawrence et al. |
| 2013/0184436 A1 | 7/2013 | Wang et al. |
| 2013/0281485 A1 | 10/2013 | Lampe et al. |
| 2013/0287688 A1 | 10/2013 | Jain et al. |

FOREIGN PATENT DOCUMENTS

| CN | 103254172 A | 8/2013 |
| EP | 2512239 A1 | 10/2012 |
| WO | WO 2005/085469 A3 | 11/2005 |
| WO | WO 2005/085466 A3 | 1/2006 |
| WO | WO 2008/077057 A3 | 8/2008 |
| WO | WO 2011/13070 A3 | 3/2012 |
| WO | WO 2013/112722 A1 | 8/2013 |

OTHER PUBLICATIONS

The Medicinenet webage for heart disease, https://www.medicinenet.com/stress_and_heart_disease/article.htm#what_if_sleep_problems_are_contributing_to_my_stress, downloaded Aug. 30, 2018.*
Liao, James K. et al, "Rho kinase (rock) inhibitors." J. Cardiovasc. Pharmacol. (2007) 50(1) p. 17-24.*
Amano, M., et al. "The COOH Terminus of Rho-kinase Negatively Regulates Rho-kinase Activity." *Journal of Biological Chemistry*, 274(45): p. 32418-32424, 1999.
Chang, J., "Activation of Rho associated coiled-coiled protein kinase 1 (ROCK-1) by caspase-3 cleavage." *Proc Natl Acad Sci U S A*, 2006.
Chen, X-Q., et al., "Characterization of RhoA-binding Kinase ROK(E± Implication of the Pleckstrin Homology Domain in ROK(E± Function Using Region-specific Antibodies." *Journal of Biological Chemistry*, 277(15): p. 12680-12688, 2002.
Dvorsky, R., L., et al., "Structural Insights into the Interaction of ROCKI with the Switch Regions of RhoA." *Journal of Biological Chemistry*, 279(8): p. 7098-7104, 2004.
Haudek, S.B., et al., "Rho kinase-1 mediates cardiac fibrosis by regulating fibroblast precursor cell differentiation." *Cardiovascular Research*, 83(3): p. 511-518, 2009.
(Continued)

*Primary Examiner* — Fred H Reynolds
(74) *Attorney, Agent, or Firm* — Parker Highlander PLLC

(57) ABSTRACT

The present disclosure describes peptide inhibitors of Rho-associtated-kinase (ROCK) and their use in treating disorders including heart failure, the leading cause of combined morbidity and mortality in the United States. An inhibitory polypeptide blocks ROCK1 activity in the presence of 1 mM ATP. The binding epitope on ROCK1 was mapped using chemical cross-linking to the Activation Loop, a novel locus identifying a new class of inhibitory drugs. The peptides described will be useful against a number of important diseases such as heart disease, pulmonary hypertension, arterial hypertension, glaucoma management, insulin resistance, kidney disease, hemolytic anemia, stroke, ischemia reperfusion injury, or acute myeloid leukemia.

15 Claims, 12 Drawing Sheets

Specification includes a Sequence Listing.

(56) References Cited

OTHER PUBLICATIONS

International Search Report and Written Opinion issued in International Application No. PCT/US2015/053503 dated Jan. 4, 2016.
Ishizaki, T., et al., "The small GTP-binding protein Rho binds to and activates a 160 kDa Ser/Thr protein kinase homologous to myotonic dystrophy kinase." *EMBO J*, 15(8): p. 1885-1893, 1996.
Jacobs, M., et al., "The Structure of Dimeric ROCK I Reveals the Mechanism for Ligand Selectivity." *Journal of Biological Chemistry*, 281(1): p. 260-268, 2006.
Nolen et al., "Regulation of Protein Kinases: Controlling Activity through Activation Segment Conformation." *Molecular Cell*, 15(5): p. 661-675, 2004.
Shimizu, T. et al., "Parallel Coiled-coil Association of the RhoA-binding Domain in Rho-kinase." *Journal of Biological Chemistry*, 278(46): p. 46046-46051, 2003.
Wei, L., et al., "Inhibition of Rho family GTPases by Rho GDP dissociation inhibitor disrupts cardiac morphogenesis and inhibits cardiomyocyte proliferation." *Development*, 129(7): p. 1705-1714, 2002.
Wei, L., et al., "Disruption of Rho signaling results in progressive atrioventricular conduction defects while ventricular function remains preserved." *FASEB J*, 18(7): p. 857-859, 2004.
Yamaguchi, H. et al., "Molecular Mechanism for the Regulation of Rho-Kinase by Dimerization and Its Inhibition by Fasudil." *Structure*, 14(3): p. 589-600, 2006.
Zhang, Y.M., et al., "Targeted deletion of ROCK1 protects the heart against pressure overload by inhibiting reactive fibrosis." *FASEB J*, 20(7): p. 916-925, 2006.

\* cited by examiner

| | | SEQ ID NO: |
|---|---|---|
| Pep25-1 | H-STAVRS-NH2 | 2 |
| Pep25-2 | H-ERTYS-NH2 | 3 |
| Pep25-3 | H-YSPST-NH2 | 4 |
| Pep25-4 | H-ERTYSPSTAVRS-NH2 | 49 |
| Pep25-5 | H-ERTYSPSTAVRA-NH2 | 50 |
| Pep25-6 | H-ERTYSPSTAVAS-NH2 | 51 |
| Pep25-7 | H-ERTYSPSTAARS-NH2 | 52 |
| Pep25-8 | H-ERTYSPSAAVRS-NH2 | 53 |
| Pep25-9 | H-ERTYSPATAVRS-NH2 | 54 |
| Pep25-10 | H-ERTYSASTAVRS-NH2 | 55 |
| Pep25-11 | H-ERTYAPSTAVRS-NH2 | 56 |
| Pep25-12 | H-ERTASPSTAVRS-NH2 | 57 |
| Pep25-13 | H-ERAYSPSTAVRS-NH2 | 58 |
| Pep25-14 | H-EATYSPSTAVRS-NH2 | 59 |
| Pep25-15 | H-ARTYSPSTAVRS-NH2 | 60 |
| Pep25-Ref | H-AYSPST-NH2 | 61 |
| Pep25-A | H-AAYSPST-NH2 | 62 |
| Pep25-F | H-FAYSPST-NH2 | 63 |
| Pep25-E | H-EAYSPST-NH2 | 64 |
| Pep25-K | H-KAYSPST-NH2 | 65 |
| Pep25-S | H-SAYSPST-NH2 | 66 |
| Pep25-P | H-PAYSPST-NH2 | 67 |
| Pep25-P1 | RAYSPSA | 68 |
| Pep25-P2 | ERTYSPS | 69 |
| Pep25-P3 | ERAYSPS | 70 |
| Pep25-P4 | ERTASPS | 71 |
| Pep25-P5 | ERDYSPS | 72 |
| Pep25-P6 | ERAYSPSA | 73 |

FIG. 7

SEQUENCE LISTING

```
<160> NUMBER OF SEQ ID NOS: 74

<210> SEQ ID NO 1
<211> LENGTH: 4
<212> TYPE: PRT
<213> ORGANISM: Artificial sequence
<220> FEATURE:
<223> OTHER INFORMATION: Synthetic peptide

<400> SEQUENCE: 1

Tyr Ser Pro Ser
1

<210> SEQ ID NO 2
<211> LENGTH: 6
<212> TYPE: PRT
<213> ORGANISM: Artificial sequence
<220> FEATURE:
<223> OTHER INFORMATION: Synthetic peptide

<400> SEQUENCE: 2

Ser Thr Ala Val Arg Ser
1               5

<210> SEQ ID NO 3
<211> LENGTH: 5
<212> TYPE: PRT
<213> ORGANISM: Artificial sequence
<220> FEATURE:
<223> OTHER INFORMATION: Synthetic peptide

<400> SEQUENCE: 3

Glu Arg Thr Tyr Ser
1               5

<210> SEQ ID NO 4
<211> LENGTH: 5
<212> TYPE: PRT
<213> ORGANISM: Artificial sequence
<220> FEATURE:
<223> OTHER INFORMATION: Synthetic peptide
```

<400> SEQUENCE: 4

Tyr Ser Pro Ser Thr
1               5

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

```
<210> SEQ ID NO 15
<400> SEQUENCE: 15
000

<210> SEQ ID NO 16
<400> SEQUENCE: 16
000

<210> SEQ ID NO 17
<400> SEQUENCE: 17
000

<210> SEQ ID NO 18
<400> SEQUENCE: 18
000

<210> SEQ ID NO 19
<400> SEQUENCE: 19
000

<210> SEQ ID NO 20
<400> SEQUENCE: 20
000

<210> SEQ ID NO 21
<400> SEQUENCE: 21
000

<210> SEQ ID NO 22
<400> SEQUENCE: 22
000

<210> SEQ ID NO 23
<400> SEQUENCE: 23
000

<210> SEQ ID NO 24
<400> SEQUENCE: 24
000

<210> SEQ ID NO 25
<400> SEQUENCE: 25
000
```

```
<210> SEQ ID NO 26
<400> SEQUENCE: 26
000

<210> SEQ ID NO 27
<400> SEQUENCE: 27
000

<210> SEQ ID NO 28
<400> SEQUENCE: 28
000

<210> SEQ ID NO 29
<400> SEQUENCE: 29
000

<210> SEQ ID NO 30
<400> SEQUENCE: 30
000

<210> SEQ ID NO 31
<400> SEQUENCE: 31
000

<210> SEQ ID NO 32
<400> SEQUENCE: 32
000

<210> SEQ ID NO 33
<400> SEQUENCE: 33
000

<210> SEQ ID NO 34
<400> SEQUENCE: 34
000

<210> SEQ ID NO 35
<400> SEQUENCE: 35
000

<210> SEQ ID NO 36
<400> SEQUENCE: 36
000
```

```
<210> SEQ ID NO 37
<400> SEQUENCE: 37
000

<210> SEQ ID NO 38
<400> SEQUENCE: 38
000

<210> SEQ ID NO 39
<400> SEQUENCE: 39
000

<210> SEQ ID NO 40
<400> SEQUENCE: 40
000

<210> SEQ ID NO 41
<400> SEQUENCE: 41
000

<210> SEQ ID NO 42
<400> SEQUENCE: 42
000

<210> SEQ ID NO 43
<400> SEQUENCE: 43
000

<210> SEQ ID NO 44
<400> SEQUENCE: 44
000

<210> SEQ ID NO 45
<400> SEQUENCE: 45
000

<210> SEQ ID NO 46
<400> SEQUENCE: 46
000

<210> SEQ ID NO 47
<400> SEQUENCE: 47
000
```

```
<210> SEQ ID NO 48
<400> SEQUENCE: 48

000

<210> SEQ ID NO 49
<211> LENGTH: 12
<212> TYPE: PRT
<213> ORGANISM: Artificial sequence
<220> FEATURE:
<223> OTHER INFORMATION: Synthetic peptide

<400> SEQUENCE: 49

Glu Arg Thr Tyr Ser Pro Ser Thr Ala Val Arg Ser
1               5                   10

<210> SEQ ID NO 50
<211> LENGTH: 12
<212> TYPE: PRT
<213> ORGANISM: Artificial sequence
<220> FEATURE:
<223> OTHER INFORMATION: Synthetic peptide

<400> SEQUENCE: 50

Glu Arg Thr Tyr Ser Pro Ser Thr Ala Val Arg Ala
1               5                   10

<210> SEQ ID NO 51
<211> LENGTH: 12
<212> TYPE: PRT
<213> ORGANISM: Artificial sequence
<220> FEATURE:
<223> OTHER INFORMATION: Synthetic peptide

<400> SEQUENCE: 51

Glu Arg Thr Tyr Ser Pro Ser Thr Ala Val Ala Ser
1               5                   10

<210> SEQ ID NO 52
<211> LENGTH: 12
<212> TYPE: PRT
<213> ORGANISM: Artificial sequence
<220> FEATURE:
<223> OTHER INFORMATION: Synthetic peptide

<400> SEQUENCE: 52

Glu Arg Thr Tyr Ser Pro Ser Thr Ala Ala Arg Ser
1               5                   10

<210> SEQ ID NO 53
<211> LENGTH: 12
<212> TYPE: PRT
<213> ORGANISM: Artificial sequence
<220> FEATURE:
<223> OTHER INFORMATION: Synthetic peptide

<400> SEQUENCE: 53

Glu Arg Thr Tyr Ser Pro Ser Ala Ala Val Arg Ser
1               5                   10

<210> SEQ ID NO 54
<211> LENGTH: 12
<212> TYPE: PRT
<213> ORGANISM: Artificial sequence
<220> FEATURE:
<223> OTHER INFORMATION: Synthetic peptide
```

```
<400> SEQUENCE: 54

Glu Arg Thr Tyr Ser Pro Ala Thr Ala Val Arg Ser
1               5                   10

<210> SEQ ID NO 55
<211> LENGTH: 12
<212> TYPE: PRT
<213> ORGANISM: Artificial sequence
<220> FEATURE:
<223> OTHER INFORMATION: Synthetic peptide

<400> SEQUENCE: 55

Glu Arg Thr Tyr Ser Ala Ser Thr Ala Val Arg Ser
1               5                   10

<210> SEQ ID NO 56
<211> LENGTH: 12
<212> TYPE: PRT
<213> ORGANISM: Artificial sequence
<220> FEATURE:
<223> OTHER INFORMATION: Synthetic peptide

<400> SEQUENCE: 56

Glu Arg Thr Tyr Ala Pro Ser Thr Ala Val Arg Ser
1               5                   10

<210> SEQ ID NO 57
<211> LENGTH: 12
<212> TYPE: PRT
<213> ORGANISM: Artificial sequence
<220> FEATURE:
<223> OTHER INFORMATION: Synthetic peptide

<400> SEQUENCE: 57

Glu Arg Thr Ala Ser Pro Ser Thr Ala Val Arg Ser
1               5                   10

<210> SEQ ID NO 58
<211> LENGTH: 12
<212> TYPE: PRT
<213> ORGANISM: Artificial sequence
<220> FEATURE:
<223> OTHER INFORMATION: Synthetic peptide

<400> SEQUENCE: 58

Glu Arg Ala Tyr Ser Pro Ser Thr Ala Val Arg Ser
1               5                   10

<210> SEQ ID NO 59
<211> LENGTH: 12
<212> TYPE: PRT
<213> ORGANISM: Artificial sequence
<220> FEATURE:
<223> OTHER INFORMATION: Synthetic peptide

<400> SEQUENCE: 59

Glu Ala Thr Tyr Ser Pro Ser Thr Ala Val Arg Ser
1               5                   10

<210> SEQ ID NO 60
<211> LENGTH: 12
<212> TYPE: PRT
<213> ORGANISM: Artificial sequence
<220> FEATURE:
<223> OTHER INFORMATION: Synthetic peptide
```

```
<400> SEQUENCE: 60

Ala Arg Thr Tyr Ser Pro Ser Thr Ala Val Arg Ser
1               5                   10

<210> SEQ ID NO 61
<211> LENGTH: 6
<212> TYPE: PRT
<213> ORGANISM: Artificial sequence
<220> FEATURE:
<223> OTHER INFORMATION: Synthetic peptide

<400> SEQUENCE: 61

Ala Tyr Ser Pro Ser Thr
1               5

<210> SEQ ID NO 62
<211> LENGTH: 7
<212> TYPE: PRT
<213> ORGANISM: Artificial sequence
<220> FEATURE:
<223> OTHER INFORMATION: Synthetic peptide

<400> SEQUENCE: 62

Ala Ala Tyr Ser Pro Ser Thr
1               5

<210> SEQ ID NO 63
<211> LENGTH: 7
<212> TYPE: PRT
<213> ORGANISM: Artificial sequence
<220> FEATURE:
<223> OTHER INFORMATION: Synthetic peptide

<400> SEQUENCE: 63

Phe Ala Tyr Ser Pro Ser Thr
1               5

<210> SEQ ID NO 64
<211> LENGTH: 7
<212> TYPE: PRT
<213> ORGANISM: Artificial sequence
<220> FEATURE:
<223> OTHER INFORMATION: Synthetic peptide

<400> SEQUENCE: 64

Glu Ala Tyr Ser Pro Ser Thr
1               5

<210> SEQ ID NO 65
<211> LENGTH: 7
<212> TYPE: PRT
<213> ORGANISM: Artificial sequence
<220> FEATURE:
<223> OTHER INFORMATION: Synthetic peptide

<400> SEQUENCE: 65

Lys Ala Tyr Ser Pro Ser Thr
1               5

<210> SEQ ID NO 66
<211> LENGTH: 7
<212> TYPE: PRT
<213> ORGANISM: Artificial sequence
<220> FEATURE:
<223> OTHER INFORMATION: Synthetic peptide
```

```
<400> SEQUENCE: 66

Ser Ala Tyr Ser Pro Ser Thr
1               5

<210> SEQ ID NO 67
<211> LENGTH: 7
<212> TYPE: PRT
<213> ORGANISM: Artificial sequence
<220> FEATURE:
<223> OTHER INFORMATION: Synthetic peptide

<400> SEQUENCE: 67

Pro Ala Tyr Ser Pro Ser Thr
1               5

<210> SEQ ID NO 68
<211> LENGTH: 7
<212> TYPE: PRT
<213> ORGANISM: Artificial sequence
<220> FEATURE:
<223> OTHER INFORMATION: Synthetic peptide

<400> SEQUENCE: 68

Arg Ala Tyr Ser Pro Ser Ala
1               5

<210> SEQ ID NO 69
<211> LENGTH: 7
<212> TYPE: PRT
<213> ORGANISM: Artificial sequence
<220> FEATURE:
<223> OTHER INFORMATION: Synthetic peptide

<400> SEQUENCE: 69

Glu Arg Thr Tyr Ser Pro Ser
1               5

<210> SEQ ID NO 70
<211> LENGTH: 7
<212> TYPE: PRT
<213> ORGANISM: Artificial sequence
<220> FEATURE:
<223> OTHER INFORMATION: Synthetic peptide

<400> SEQUENCE: 70

Glu Arg Ala Tyr Ser Pro Ser
1               5

<210> SEQ ID NO 71
<211> LENGTH: 7
<212> TYPE: PRT
<213> ORGANISM: Artificial sequence
<220> FEATURE:
<223> OTHER INFORMATION: Synthetic peptide

<400> SEQUENCE: 71

Glu Arg Thr Ala Ser Pro Ser
1               5

<210> SEQ ID NO 72
<211> LENGTH: 7
<212> TYPE: PRT
<213> ORGANISM: Artificial sequence
<220> FEATURE:
<223> OTHER INFORMATION: Synthetic peptide
```

```
<400> SEQUENCE: 72

Glu Arg Asp Tyr Ser Pro Ser
1               5

<210> SEQ ID NO 73
<211> LENGTH: 8
<212> TYPE: PRT
<213> ORGANISM: Artificial sequence
<220> FEATURE:
<223> OTHER INFORMATION: Synthetic peptide

<400> SEQUENCE: 73

Glu Arg Ala Tyr Ser Pro Ser Ala
1               5

<210> SEQ ID NO 74
<211> LENGTH: 8
<212> TYPE: PRT
<213> ORGANISM: Artificial sequence
<220> FEATURE:
<223> OTHER INFORMATION: Synthetic peptide

<400> SEQUENCE: 74

Met Asn Lys Glu Gly Met Val Arg
1               5
```

RHO ASSOCIATED KINASE (ROCK) INHIBITORS AND THEIR USE IN TREATING DISEASE

The present application a national phase application under 35. U.S.C. § 371 of International Application No. PCT/US2015/053503, filed Oct. 1, 2015, and claims the priority benefit of U.S. Provisional Application No. 62/060,336, filed Oct. 6, 2014, the entire contents of each of which are incorporated herein by reference

BACKGROUND OF THE INVENTION

1. Field of the Invention

The present disclosure relates generally to the fields of cardiology, pathology and molecular biology. More particularly, it concerns the identification of peptide inhibitors of Rho-associated-kinase (ROCK) has two isoforms, ROCK1 (p160ROCK, ROKb), and ROCK2 (ROKa) that treat heart disease as well as other diseases.

2. Description of Related Art

Heart disease and its manifestations, including coronary artery disease, myocardial infarction, congestive heart failure and cardiac hypertrophy, clearly presents a major health risk in the United States today. The cost to diagnose, treat and support patients suffering from these diseases is well into the billions of dollars. Two particularly severe manifestations of heart disease are myocardial infarction and cardiac hypertrophy. With respect to myocardial infarction, typically an acute thrombocytic coronary occlusion occurs in a coronary artery as a result of atherosclerosis and causes myocardial cell death. Because cardiomyocytes, the heart muscle cells, are terminally differentiated and generally incapable of cell division, they are generally replaced by scar tissue when they die during the course of an acute myocardial infarction. Scar tissue is not contractile, fails to contribute to cardiac function, and often plays a detrimental role in heart function by expanding during cardiac contraction, or by increasing the size and effective radius of the ventricle, for example, becoming hypertrophic. Although, initial collagen deposition is required for infarct healing and to prevent cardiac rupture, the continuous production of collagen by fibroblasts induces interstitial fibrosis surrounding the myocytes in the infarct borderzone and remote myocardium of the infracted heart. This fibrosis induces stiffness, diastolic dysfunction, and cardiomyocyte hypertrophy due to the increase in stress and can also lead to arrythmias.

Cardiac hypertrophy is an adaptive response of the heart to virtually all forms of cardiac disease, including those arising from hypertension, mechanical load, myocardial infarction, cardiac arrhythmias, endocrine disorders, and genetic mutations in cardiac contractile protein genes. While the hypertrophic response is initially a compensatory mechanism that augments cardiac output, sustained hypertrophy can lead to dilated cardiomyopathy (DCM), heart failure, and sudden death. In the United States, approximately half a million individuals are diagnosed with heart failure each year, with a mortality rate approaching 50%. The causes and effects of cardiac hypertrophy have been extensively documented, but the underlying molecular mechanisms have not been completely elucidated. Understanding these mechanisms is a major concern in the prevention and treatment of cardiac disease and will be crucial as a therapeutic modality in designing new drugs that specifically target cardiac hypertrophy and cardiac heart failure.

Treatment with pharmacological agents represents the primary mechanism for reducing or eliminating the manifestations of heart failure. Diuretics constitute the first line of treatment for mild-to-moderate heart failure. If diuretics are ineffective, vasodilatory agents, such as angiotensin converting enzyme (ACE) inhibitors (e.g., enalopril and lisinopril) or inotropic agent therapy (i.e., a drug that improves cardiac output by increasing the force of myocardial muscle contraction) may be used. Unfortunately, many of these standard therapies have numerous adverse effects and are contraindicated in some patients. Thus, the currently used pharmacological agents have severe shortcomings in particular patient populations. The availability of new, safe and effective agents would undoubtedly benefit patients who either cannot use the pharmacological modalities presently available, or who do not receive adequate relief from those modalities.

ROCK1 a member of the Rho kinase family (3) has been implicated in cardiac hypertrophy and ventricular remodeling by Schwartz and coworkers (2,4-7). ROCK1 knockout (ROCK1-/-) mice did not impair compensatory hypertrophic response induced by pressure overload, but exhibited reduced perivascular and interstitial fibrosis which occurs 3 weeks after the aortic banding (5). Blocking ROCK1 gene activity significantly reduced the amount of mononuclear cells that differentiated into fibroblasts by >20-fold (2). Thus, identifying new agents to inhibit ROCK1 activity could prove useful in the development of new cardiac therapies.

SUMMARY OF THE INVENTION

Thus, in accordance with the present disclosure, there is provided a pharmaceutical composition comprising (a) a peptide consisting of 4-30 residues and exhibiting the sequence YSPS (SEQ ID NO: 1) and (b) a pharmaceutically acceptable buffer, excipient or diluent. The peptide may consist of 4, 5, 6, 7, 8, 9, 10, 11, 12, 13, 14, 15, 16, 17, 18, 19, 20, 21, 22, 23, 24, 25 or 30 residues. The peptide may comprise, consist essentially of or consist of the sequence ERTYSPS (SEQ ID NO: 69) or the sequence ERTYSPSTAVRS (SEQ ID NO: 49). The peptide may further comprise one or more D-amino acid residues, or all D-amino acid residues. The peptide may comprise a membrane permibility sequence motif or be conjugated to a compound aiding in the delivery the pharmaceutical composition.

In another embodiment, there is provided a method of treating heart disease comprising administering to a subject in need thereof a pharmaceutical composition comprising (a) a peptide consisting, of 4-30 residues and exhibiting the sequence YSPS (SEQ ID NO: 1) and (h) a pharmaceutically acceptable buffer, excipient or diluent. The peptide may consist of 4, 5, 6, 7, 8, 9, 10, 11, 12, 13, 14, 15, 16, 17, 18, 19, 20, 21, 22, 23, 24, 25 or 30 residues. The peptide may comprise, consist essentially of or Consist of the sequence ERTYSPS (SEQ ID NO: 69) or the sequence ERTYSPSTAVRS (SEQ ID NO: 49). The peptide may further comprise one or more D-amino acid residues, or all D-amino acid residues.

Administering the inhibitor may be performed intramuscularly, intravenously or by direct injection into cardiac tissue, or may involve oral, transdermal, sustained release, controlled release, delayed release, suppository, or sublingual administration. The method may further comprise administering said peptide to said subject at least a second time, such as administering the peptide chronically to said subject. The peptide may be administered to said subject in a unit dose form. The method may further comprise administering to said patient a second heart disease therapy, such as a second ROCK inhibitor, a beta blocker, an ionotrope, a diuretic, ACE-1. AII antagonist, BNP, or a $Ca^{++}$ channel blocker. The second therapy may be is administered at the same time as said peptide, or either before or after said peptide.

Treating comprises improving one or more symptoms of heart failure, such as increased exercise capacity, increased cardiac ejection volume, increased cardiac ejection fraction, decreased left ventricular end diastolic pressure, decreased pulmonary capillary wedge pressure, increased cardiac output, or cardiac index, lowered pulmonary artery pressures, decreased left ventricular end systolic and diastolic dimensions, decreased left and right ventricular wall stress, decreased wall tension, increased quality of life, and decreased disease-related morbidity or mortality.

In other embodiments, there is provided:
a method of treating kidney disease comprising administering to a subject in need thereof a pharmaceutical composition comprising (a) a peptide consisting of 4-30 residues and exhibiting the sequence YSPS (SEQ ID NO: 1) and (b) pharmaceutically acceptable buffer, excipient or diluent;
a method of treating pulmonary hypertension comprising administering to a subject in need thereof a pharmaceutical composition comprising (a) a peptide consisting of 4-30 residues and exhibiting the sequence YSPS (SEQ ID NO: 1) and (b) a pharmaceutically acceptable buffer, excipient or diluent;
a method of treating arterial hypertension comprising administering to a subject in need thereof a pharmaceutical composition comprising (a) a peptide consisting of 4-30 residues and exhibiting the sequence YSPS (SEQ ID NO: 1) and (b) a pharmaceutically acceptable buffer, excipient or diluent;
a method of treating glaucoma comprising administering to a subject in need thereof a pharmaceutical composition comprising (a) a peptide consisting of 4-30 residues and exhibiting the sequence YSPS (SEQ ID NO: 1) and (b) a pharmaceutically acceptable buffer, excipient or diluent;
a method of treating acute myelogenous leukemia comprising administering to a subject in need thereof a pharmaceutical composition comprising (a) a peptide consisting of 4-30 residues and exhibiting the sequence YSPS (SEQ ID NO: 1) and (b) a pharmaceutically acceptable buffer, excipient or diluent;
a method of treating insulin resistance comprising administering to a subject in need thereof a pharmaceutical composition comprising (a) a peptide consisting of 4-30 residues and exhibiting the sequence YSPS (SEQ ID NO: 1) and (b) a pharmaceutically acceptable buffer, excipient or diluent;
a method of treating hemolytic anemia comprising administering to a subject in need thereof a pharmaceutical composition comprising (a) a peptide consisting of 4-30 residues and exhibiting the sequence YSPS (SEQ ID NO: 1) and (b) a pharmaceutically acceptable buffer, excipient or diluent;
a method of treating stroke comprising administering to a subject in need thereof a pharmaceutical composition comprising (a) a peptide consisting of 4-30 residues and exhibiting the sequence YSPS (SEQ ID NO: 1) and (b) a pharmaceutically acceptable buffer, excipient or diluent; or
a method of treating ischemia-reperfusion injury comprising administering to a subject in need thereof a pharmaceutical composition comprising (a) a peptide consisting of 4-30 residues and exhibiting the sequence YSPS (SEQ ID NO: 1) and (h) a pharmaceutically acceptable buffer, excipient or diluent.

The use of the word "a" or an when used in conjunction with the term "comprising" in the claims and/or the specification may mean "one," but it is also consistent with the meaning of "one or more," "at least one" and "one or more than one."

It is contemplated that any embodiment discussed herein, can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The invention may be better understood by reference to one or more of these drawings in combination with the detailed description of specific embodiments presented herein.

FIG. 7—Peptide25 and its derivatives. These peptides were evaluated in this ROCK inhibitor study.

DETAILED DESCRIPTION OF ILLUSTRATIVE EMBODIMENTS

Figure 1:
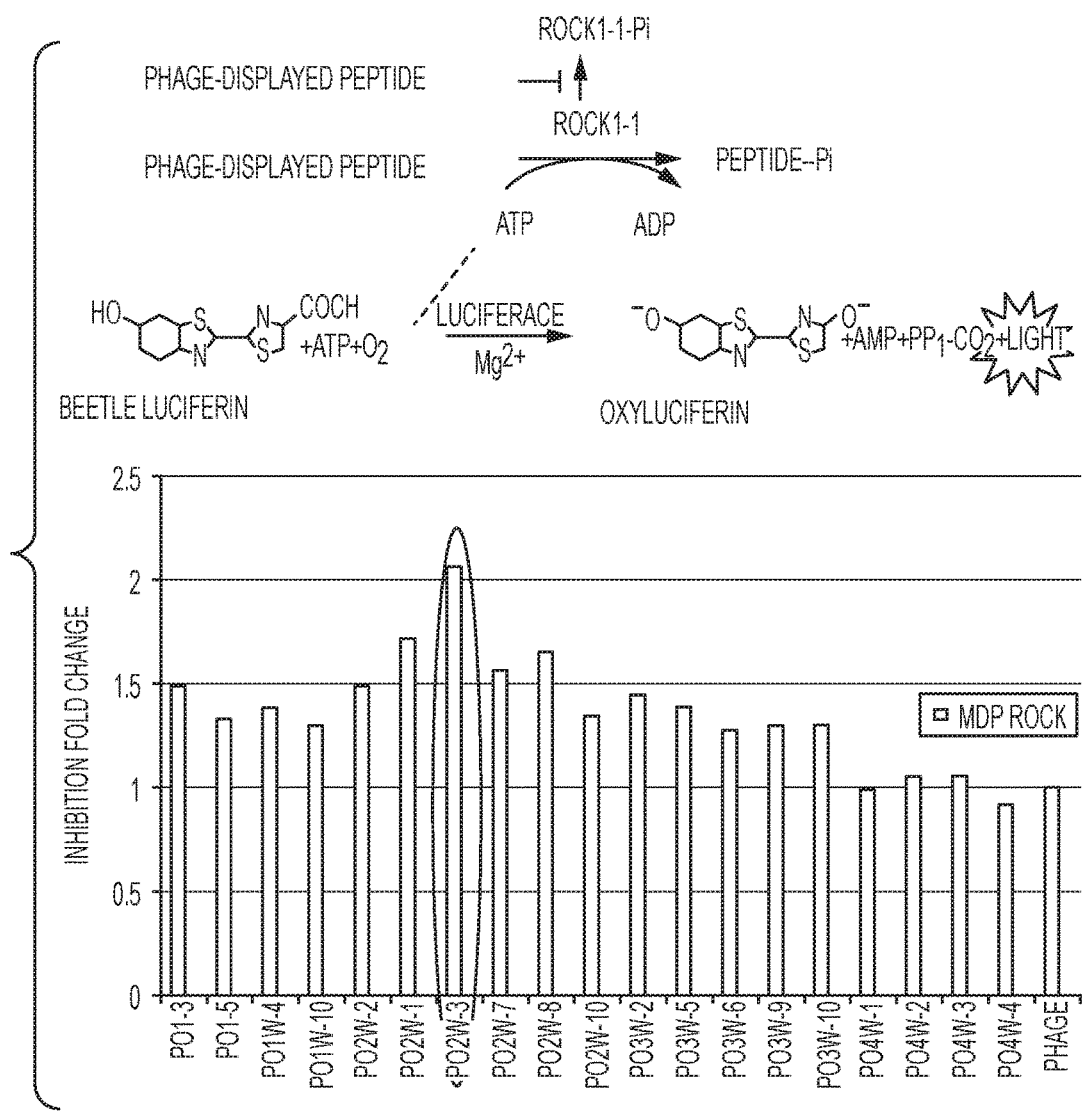
FIG. 1—Enriched phage displayed peptides that inhibit ROCK1 autophosphoryaltion. The maltose binding protein fusion protein linked to the ROCK1 kinase domain (MBP-ROCK1) was incubated with a Ph.D-12 phage display library of 12 amino acids in length (New England Biolabs, Inc).
Figure 2:
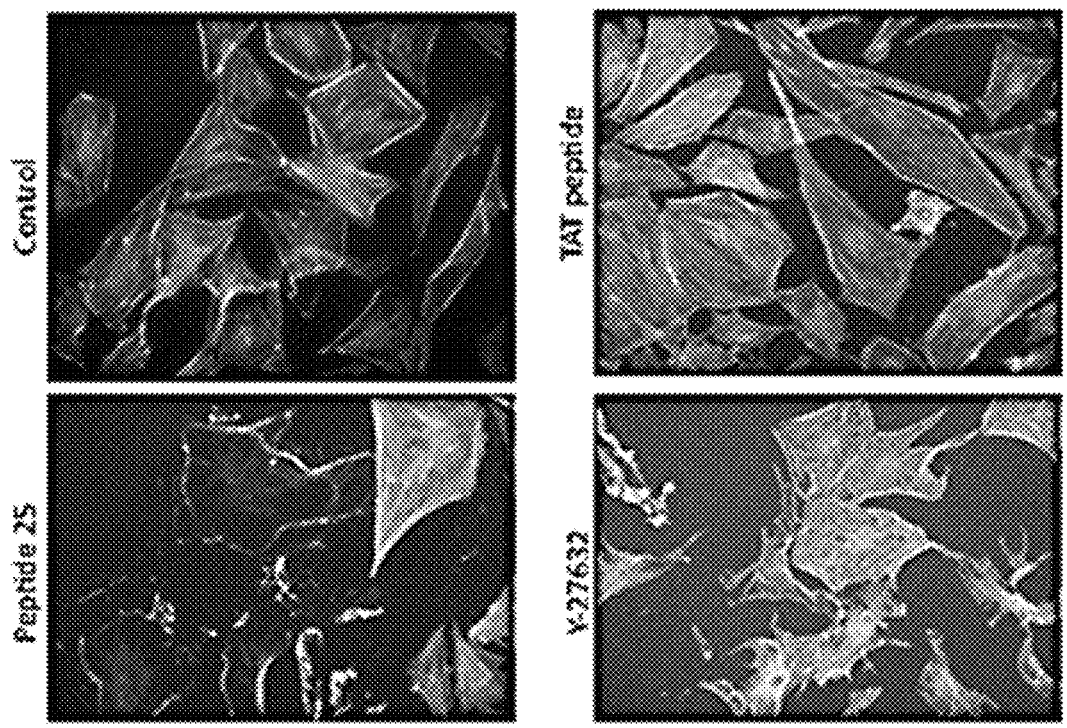
FIG. 2—TAT-end-labeled peptide25 and Y27632 melted cytoskeleton. Peptides25 was synthesized and one of which contained a fusion of the N' end terminal TAT sequence (TATpeptide25), which allows peptides and proteins easy entry into cells.
Figure 3:
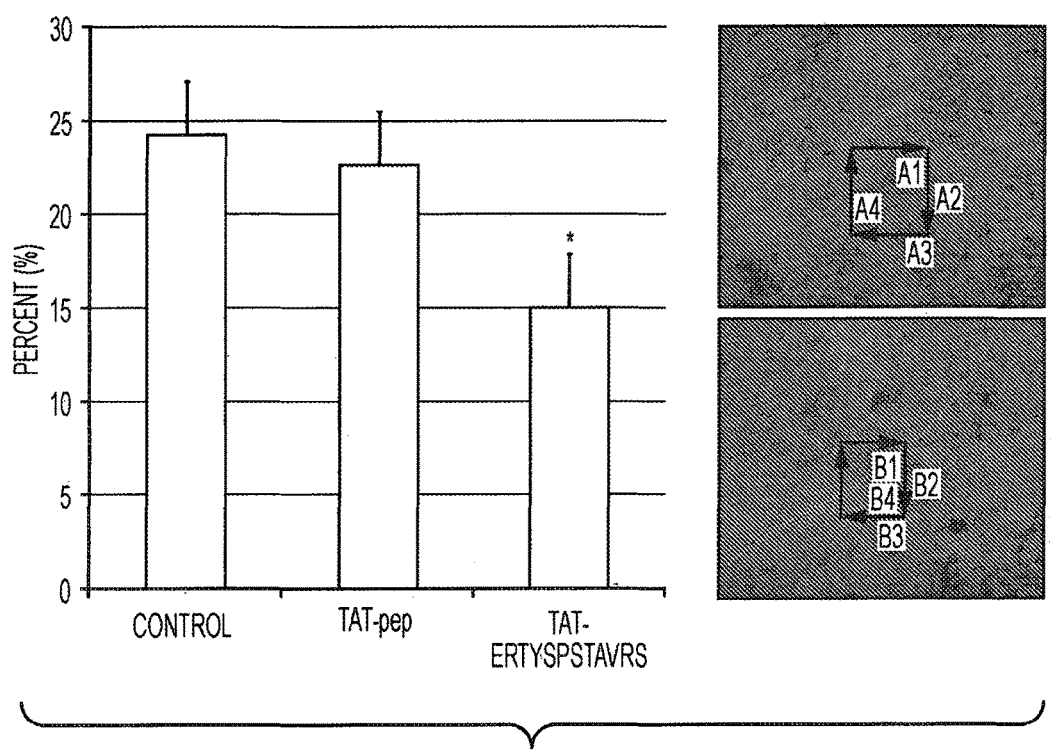
FIG. 3—Peptide25 significantly inhibits ROCK1 (mean: 15% p-value: 0.03) for 4 separate experiments with each having 3 trials for a total of 12 measurements.
Figure 4:
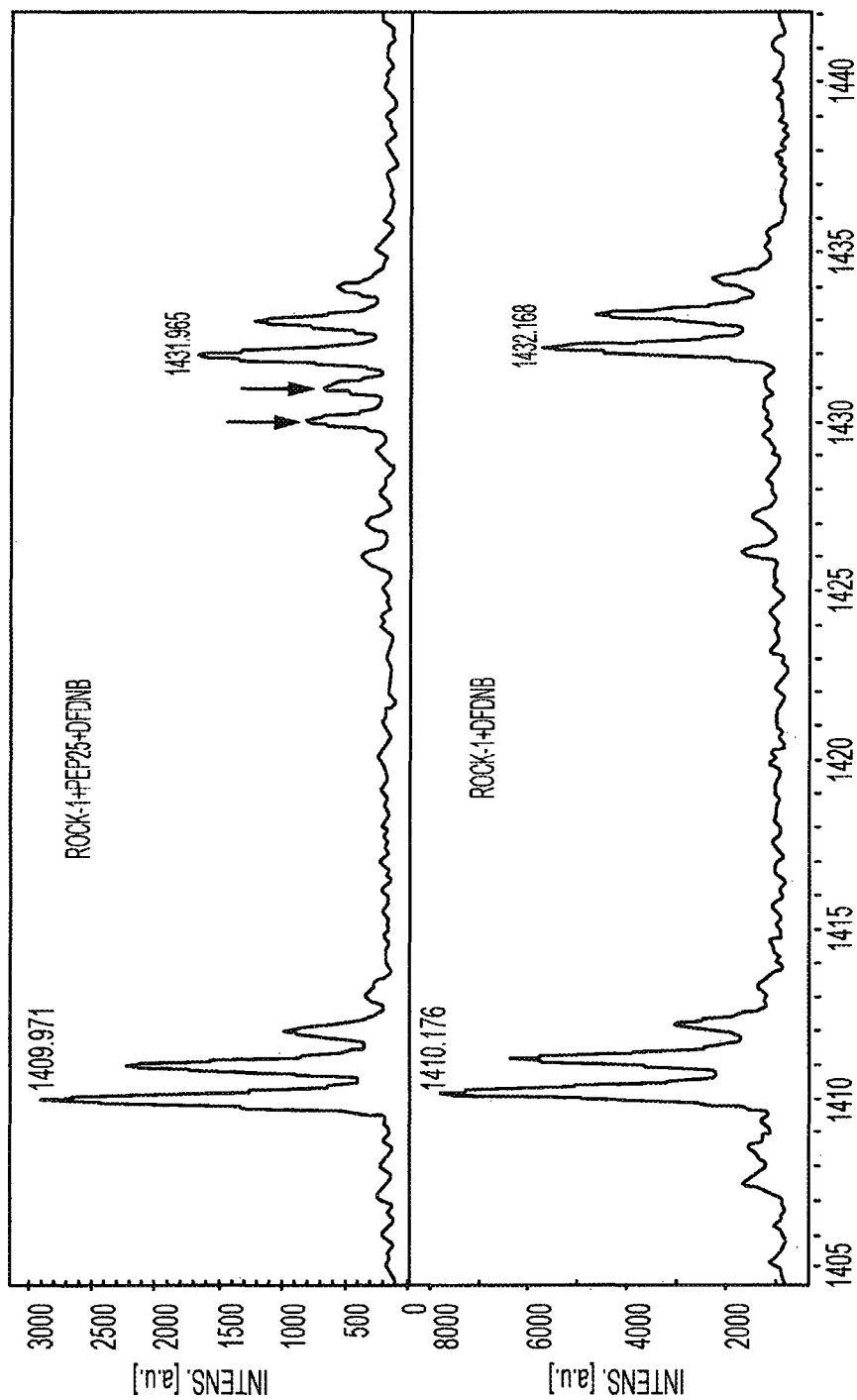
FIG. 4—Mapping peptide25 binding epitope in ROCK1 using a crosslinking reaction, trypsin digestion and mass spectroscopy. Arrows point the peak m/z 1430.02. The peaks represent the DFDNB linking peptide25 and ROCK1 segment.

Heart failure is the leading cause of combined morbidity and mortality in the United States and other developed industrial nations, with an estimated two-year mortality of 30-50% for the patients with advanced disease (Narula a al., 2001). Pathophysiological cardiac hypertrophy is accompanied by reactive fibrosis and remodeling. Recently, highly proliferative CD34+/CD45+ fibroblasts derived from monocytic, blood-borne precursor cells were shown to play a critical role in the development of fibrosis in a mouse model of ischaemic/reperfusion ardiomyopathy (I/RC) similar to human heart, disease (Haudek et al., 2009). The differentiation of human monocytes into fibroblasts in vitro occurs after transendothelial migration (TEM) induced by monocyte chemoattractant protein 1 (MCP-1).

As mentioned above, ROCK1 has been implicated in cardiac hypertrophy and ventricular remodeling (Haudek at al., 2009; Chang, 2006; Zhang et al., 2006 Wei et al., 2004; Wei et al., 2002). ROCK1 knockout (ROCK1−/−) mice did not impair compensatory hypertrophic response induced by pressure overload, but exhibited reduced perivascular and interstitial fibrosis which occurs 3 weeks after the aortic banding (Zhang at al., 2006). Blocking ROCK1 gene activity significantly reduced the amount of mononuclear cells that differentiated into fibroblasts by >20-fold (Haudek et al., 2009).

In this study, the inventors focused on Rho-associated-kinase (ROCK) downstream effectors of Rho which have two isoforms, ROCK1 (p160ROCK, ROKb), ROCK2 (ROKa), This serine-threonine kinase is composed of 3 domains including the N-terminal catalytic domain, followed by the coil-coiled and Rho-binding domain (RBD) and then the C-terminal Pleckstrin homology domain (PH domain, (T Ishizaki et al., 1996; Jacobs et al., 2006; Yamaguchi et al., 2006)). ROCK is activated by Rho-GTP at the RBD domain by putatively displacing the PH domain. The catalytic domain of ROCK is inhibited by the C-terminal Rho Binding Domain (RBD) and Pleckstrin-Homology domain (PH domain) from residues based on Rho Binding and PH domain fragment that blocked stress fiber and focal adhesion formation in NIH 3T3 Cells (Amano et al, 1999; Chen et al., 2002). In addition, The Rho-binding Domain residues 934 to 1015 binds RhoAGTP (Aniano et al., 1999; Shimizo et al., 2003; Dvorsky et al 2004).

ROCK may be activated in heart disease by low levels of activated Caspase 3 which cleaves ROCK1, releasing the PH domain causing super-activated ROCK1, which may further enhance heart disease and fibrosis (Chang, 2006). The inventors previously found that in failing human hearts, Rho-associated kinase 1 (ROCK1) is processed by caspase-3 into an active isoform, ROCKΔ1. The inventors generated transgenic mice expressing ROCKΔ1 in cardiomyocytes to mimic the situation observed in human heart disease, whereas an additional kinase-deficient mouse was generated as a control. The ROCKΔ1 transgenic mice developed, fibrotic cardiomyopathy with diastolic dysfunction. Transgenic hearts displayed activated TGFβ1 and NP-κB signaling and a release of a subset of cytokines and were susceptible to angiotensin II stress. Treatment with a Rho kinase inhibitor attenuated the fibrotic phenotype. Cardiac fibroblasts differentiated into myofibroblasts when cocultured with transgenic cardiomyocytes but not with wild-type cardiomyocytes.

These and other aspects of the disclosure are described in detail below.

I. ROCK

Rho-associated-kinases (ROCK) are down-stream effectors of Rho and have two isoforms, ROCK1 (p160ROCK, ROKb) and ROCK-2 (ROKa). This serine-threonine kinase is composed of 3 domains including the N-terminal catalytic domain, following by the coil-coiled and Rho-binding-binding domains and then the C-terminal Pleckstrin homology domain (PH domain). ROCK is activated by Rho-GTP at the RBD domain by displacement of the PH domain, an autoregulatory inhibitor of kinase domain. In many preclinical models of cardiovascular diseases, including vasospasm, arteriosclerosis, hypertension, pulmonary hypertension, stroke, ischemia-reperfusion injury, and heart failure, ROCK inhibitors have shown a remarkable efficacy in reducing vascular smooth muscle cell hypercontraction, endothelial dysfunction, inflammatory cell recruitment, vascular remodeling, and cardiac remodeling. The development of more potent and specific inhibitors of ROCK signaling is of high importance in treating many human diseases.

II. PEPTIDE INHIBITORS

A. Structure

The present invention contemplates the design, production and use of various ROCK inhibitory peptides. The structural features of these peptides are as follows. First, the peptides will generally have no more than 50 consecutive residues, and more particularly be 30 residues or less. Thus, the term "a peptide having no more than 30 consecutive residues," even when including the term "comprising," cannot be understood to comprise a greater number of residues. Second, the peptides will contain the motifs responsible for interaction ROCK1. In general, the peptides will have, at a minimum, YSPS.

In general, the peptides will be 4-30 residues. The overall length may be 4, 5, 6, 7, 8, 9, 10, 11, 12, 13, 14, 15, 16, 17, 18, 19, 20, 21, 22, 23, 24, 25, 26, 27, 28, 29, or 30 residues. Ranges of peptide length of 4-30 residues, 5-30 residues, 6-30 residues, 7-30 residues, 12-30 residues, 15-30, residues, 4-20 residues, 5-20 residues. 6-20 residues, 7-20 residues, 12-20 residues, and 10-25 residues are contemplated.

The present invention may utilize L-configuration amino acids, D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary).

One form of an peptide is a retro-inverso peptide. Retro-inverso modification of naturally-occurring polypeptides involves the synthetic assemblage of amino acids with α-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

As mentioned above, the present invention contemplates fusing or conjugating a cell delivery domain (also called a cell delivery vector, or cell transduction domain). Such domains are well known in the art and are generally characterized as short amphipathic or cationic peptides and peptide derivatives, often containing multiple lysine and arginine resides (Fischer, 2007). Of particular interest are the Tat sequence, poly-D-Arg and poly-D-Lys sequences (e.g., dextrorotary residues, eight residues in length).

Also as mentioned above, peptides modified for in vivo use by the addition, at the amino- and/or carboxyl-terminal ends, of a blocking agent to facilitate survival of the peptide in vivo are contemplated. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. These agents can be added either chemically during the synthesis of the peptide, or by recombinant DNA technology by methods familiar in the art. Alternatively, blocking agents such as pyroglutamic acid or other molecules known in the art can be attached to the amino and/or carboxyl-terminal residues.

B. Synthesis

It will be advantageous to produce peptides using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the 20 standard amino acids can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

C. Linkers

Linkers or cross-linking agents may be used to fuse peptides to other proteinaceous sequences. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidino-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic in residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

Another use of linkers in the context of peptides as therapeutics is the so-called "Stapled Peptide" technology of Aileron Therapeutics. The general approach for "stapling" a peptide is that two key residues within the peptide are modified by attachment of linkers through the amino acid side chains. Once synthesized, the linkers are connected through a catalyst, thereby creating a bridge the physically constrains the peptide into its native α-helical shape. In addition to helping retain the native structure needed to interact with a target molecule, this conformation also provides stability against peptidases as well as cell-permeating properties. U.S. Pat. Nos. 7,192,713 and 7,183,059, describing this technology, are hereby incorporated by reference. See also Schafmeister et al., 2000.

D. Conjugation

Conjugation with many forms of materials may also be used. Many applications of compounds can entail the invention attached to silicon beads, gold nano particles, or any other suitable material to enhance transport and uptake of the invented peptides or their derivatives. These include heterogenous compounds that include the invention, linkers as described before, the conjugated material such as silicon beads, additional linkages to other signaling proteinaceous sequences that direct the compound to sites of interest. Examples include conjugations with Lymphocyte function-associated antigen to direct transport to sites of inflammation or the use of cell marker to direct transport to cardiac tissues.

III. METHODS OF TREATING DISEASE STATES

The present invention provides methods of treating various disease states by administering to a subject peptides of the present disclosure. For the purposes of the present application, treatment comprises reducing one or more of the symptoms of associated with the disease states discussed below. Any level of improvement will be considered treatment, and there is no requirement for a particular level of improvement or a "cure." It is also sufficient in treatment that symptoms be stabilized, i.e., that the disease condition will not worsen.

A. Pathological Conditions

Heart Disease.

Heart failure is one of the leading causes of morbidity and mortality in the world. In the U.S. alone, estimates indicate that 3 million people are currently living with cardiomyopathy and another 400,000 are diagnosed on a yearly basis. Dilated cardiomyopathy (DCM), also referred to as "congestive cardiomyopathy," is the most common form of the cardiomyopathies and has an estimated prevalence of nearly 40 per 100,000 individuals (Durand et al., 1995). Approximately half of DCM cases are idiopathic, and of these, familial dilated cardiomyopathy has been indicated as representing approximately 20%. The remaining half of DCM cases are associated with known disease processes, such as untreated hypertension or valvular heart disease, as an end-stage condition. Furthermore, serious myocardial damage can result from certain drugs used in cancer chemotherapy (e.g., doxorubicin and daunoribucin). In addition, many DCM patients are chronic alcoholics. Fortunately, for these patients, the progression of myocardial dysfunction may be stopped or reversed if alcohol consumption is reduced or stopped early in the course of disease. Peripartum cardiomyopathy is another idiopathic form of DCM, as is disease associated with infectious sequelae. In sum, cardiomyopathies including inherited or acquired DCM, are significant public health problems.

Current medical management of cardiac hypertrophy in the setting of a cardiovascular disorder includes the use of at least two types of drugs: inhibitors of the rennin-angiotension system, and β-adrenergic blocking agents (Bristow, 1999). Therapeutic agents to treat pathologic hypertrophy in the setting of heart failure include angiotensin II converting enzyme (ACE) inhibitors and β-adrenergic receptor blocking agents (Eichhorn and Bristow, 1996). Other pharmaceutical agents that have been disclosed for treatment of cardiac hypertrophy include angiotensin II receptor antagonists (U.S. Pat. No. 5,604,251) and neuropeptide Y antagonists (WO 98/33791). Despite currently available pharmaceutical compounds, prevention and treatment of cardiac hypertrophy, and subsequent heart failure, continue to present a therapeutic challenge.

Non-pharmacological treatment is primarily used as an adjunct to pharmacological treatment. One means of non-pharmacological treatment involves reducing the sodium in the diet. In addition, non-pharmacological treatment also entails the elimination of certain precipitating drugs, including negative inotropic agents (e.g., certain calcium channel blockers and antiarrhythmic drugs like disopyramide), cardiotoxins (e.g., amphetamines), and plasma volume expanders (e.g., nonsteroidal anti-inflammatory agents and glucocorticoids).

In one embodiment of the present invention, methods for the treatment of heart failure utilizing inhibitors as described herein. For the purposes of the present application, treatment comprises reducing one or more of the symptoms of cardiac hypertrophy, such as reduced exercise capacity, reduced blood ejection volume, increased left ventricular end diastolic pressure. Increased pulmonary capillary wedge pressure, reduced cardiac output, cardiac index, increased pulmonary artery pressures, increased left ventricular end systolic and diastolic dimensions, and increased left ventricular wall stress, wall tension and wall thickness-same for right ventricle. In addition, use of the disclosed inhibitors may delay development of year failure.

Treatment regimens would vary depending on the clinical situation. However, long term maintenance would appear to be appropriate in most circumstances. It also may be desirable treat hypertrophy with the disclosed inhibitors intermittently, such as within brief window during disease progression.

Pulmonary Hypertension.

Pulmonary hypertension (PH) is currently an incurable disease. "PH is defined by an increase in mean pulmonary arterial pressure (PAP) ≥25 mm Hg at rest, a pulmonary wedge pressure (PWP) ≤15 mm Hg and a normal or reduced cardiac output, assessed by right heart catheterization. Current treatment of PH consists of the use of conventional therapy in combination with specific treatments with continuous prostacyclin infusion or inhalation, oral phosphodiesterase-5 inhibitors and oral endothelin-1 receptor antagonists. None of these drugs, however, can be considered as an optimal treatment for PH as they mainly act as vasodilators and lack inhibitory effects on remodeling of the pulmonary vasculature. Recently, accumulating evidence showed that RhoA, and its downstream effectors, the Rho-kinases, have a preponderant role in the physiopathology of PH due to their potent effects on pulmonary arterial smooth muscle cell (SMCs) contraction and proliferation" from Duong-Quy et al., *Pharmacol Ther.* 137(3):352-64 (2013).

Arterial Hypertension.

Arterial hypertension is a major health problem, accounting for 12% of the global death rate. A large proportion of patients treated for high blood pressure do not reach target blood pressure values. The question arises if new antihypertensive drugs could improve present hypertension treatment. Rho-kinases (ROCKs) are ubiquitously expressed serine/threonine kinases and involved in a variety of cell functions. They contribute to the pathogenesis of human and experimental hypertension. Pharmacological ROCK inhibition has been shown to effectively lower blood pressure in patients and experimental animals. Progress has been made towards the understanding on how non-selective ROCK inhibitors lower arterial pressure and efforts are currently undertaken to develop ROCK inhibitors to improve their specificity and isoenzyme selectivity. If introduction of ROCK inhibitors for the treatment of high blood pressure can significantly advance currently available options of antihypertensive pharmacotherapy awaits further experimental and clinical research.

Glaucoma Management

Lowering intraocular pressure (IOP) is the only proven therapeutic intervention for glaucomatous optic neuropathy. Despite advances in laser and microsurgical techniques, medical IOP reduction remains the first-line treatment option for the majority of patients with open-angle glaucoma. Prostaglandin analogs are the most efficacious topical agents and carry a remarkable safety profile. Topical beta-blockers, alpha-agonists, and carbonic anhydrase inhibitors are often employed as adjunctive agents for further RR control. Newer preserved and nonpreserved formulations are available and appear to be less toxic to the ocular surface. Oral carbonic anhydrase inhibitors, miotic agents, and hyperosmotics are infrequently used due to a host of potentially serious adverse events. Medical therapies on the horizon include rho-kinase inhibitors.

Insulin Resistance.

Insulin's ability to activate IRS-1/PI3K/Akt signaling was greatly enhanced in adipose tissue of ROCK1(−/−) mice compared with wild-type mice. These effects resulted from the inhibitory effect of ROCK1 on insulin receptor action, as evidenced by the fact that IR tyrosine phosphorylation was abolished in ROCK1(−/−) MEF cells when ROCK1 was re-expressed. ROCK1 isoform plays an inhibitory role for the regulation of insulin sensitivity in diet-induced obesity in vivo.

Kidney Disease.

Blockade of Rho kinase with pharmacologic inhibitors ameliorates renal fibrosis and diabetic kidney disease (DKD), the underlined mechanisms remain largely unclear. The present study tested the hypothesis that ROCK1 may regulate the early development of albuminuria via the megalin/cubilin-dependent mechanism.

Hemolytic Anemia.

Using gene-targeted ROCK1-deficient mice, phenylhydrazine-induced oxidative stress model results in enhanced recovery from hemolytic anemia as well as enhanced splenic stress erythropoiesis compared with control mice. Deficiency of ROCK1 also results in enhanced survival, whereas wild-type mice die rapidly in response to stress. Enhanced survivability of ROCK1-deficient mice is associated with reduced level of reactive oxygen species.

Stroke.

A stroke, sometimes referred to as a cerebrovascular accident (CVA), cerebrovascular insult (CVI), or colloquially brain attack is the loss of brain function due to a disturbance in the blood supply to the brain. This disturbance is due to either ischemia (lack of blood flow) or hemorrhage. Ischemia is caused by either blockage of a blood vessel via thrombosis or arterial embolism, or by cerebral hypoperfusion. Hemorrhagic stroke is caused by bleeding of blood vessels of the brain, either directly into the brain parenchyma or into the subarachnoid space surrounding brain tissue. As a result, the affected area of the brain cannot function normally, which might result in an inability to move one or more limbs on one side of the body, failure to understand or formulate speech, or a vision impairment of one side of the visual field.

A stroke is a medical emergency and can cause permanent neurological damage or death. Risk factors for stroke include old age, high blood pressure, previous stroke or transient ischemic attack (TIA), diabetes, high cholesterol, tobacco smoking and atrial fibrillation. High blood pressure is the most important modifiable risk factor of stroke. Cerebrovascular disease was the second leading cause of death worldwide in 2004. An ischemic stroke is occasionally treated in a hospital with thrombolysis (also known as a "clot buster"), and some hemorrhagic strokes benefit from neurosurgery. Treatment to recover any lost function is termed stroke rehabilitation, ideally in a stroke unit and involving health professions such as speech and language therapy, physical therapy and occupational therapy. Prevention of recurrence may involve the administration of antiplatelet drugs such as aspirin and dipyridamole, control and reduction of high blood pressure, and the use of statins. Selected patients may benefit from carotid endarterectomy and the use of anticoagulants.

Ischemia Reperfusion Injury.

Reperfusion injury is the tissue damage caused when blood supply returns to the tissue after a period of ischemia or lack of oxygen. The absence of oxygen and nutrients from blood during the ischemic period creates a condition in which the restoration of circulation results in inflammation and oxidative damage through the induction of oxidative stress rather than restoration of normal function.

Reperfusion of ischemic tissues is often associated with microvascular injury, particularly due to increased permeability of capillaries and arterioles that lead to an increase of diffusion and fluid filtration across the tissues. These "activated" endothelial cells produce more reactive oxygen species but less nitric oxide following reperfusion, and the imbalance results in a subsequent inflammatory response. The inflammatory response is partially responsible for the damage of reperfusion injury. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane. Damage to the cell's membrane may in turn cause the release of more free radicals. Such reactive species may also act indirectly in redox signaling to turn on apoptosis. White blood cells may also bind to the endothelium of small capillaries, obstructing them and leading to more ischemia. Another hypothesis would be that normally, tissues contain free radical scavengers to avoid damage by oxidizing species normally contained in the blood. Ischemic tissue would have a decrease function of these scavengers because of cell injury. Once blood flow is reestablished, oxygen species contained in the blood will damage the ischemic tissue because the function of the scavengers is decreased.

Reperfusion injury plays a part in the brain's ischemic cascade, which is involved in stroke and brain trauma. Similar failure processes are involved in brain failure following reversal of cardiac arrest; control of these processes is the subject of ongoing research. Repeated bouts of ischemia and reperfusion injury also are thought to be a factor leading to the formation and failure to heal of chronic wounds such as pressure sores and diabetic foot ulcers. Continuous pressure limits blood supply and causes ischemia, and the inflammation occurs during reperfusion. As this process is repeated, it eventually damages tissue enough to cause a wound.

In prolonged ischemia (60 minutes or more), hypoxanthine is formed as breakdown product of ATP metabolism. The enzyme xanthine dehydrogenase acts in reverse, that is as a xanthine oxidase as a result of the higher availability of oxygen. This oxidation results in molecular oxygen being converted into highly reactive superoxide and hydroxyl radicals. Xanthine oxidase also produces uric acid, which may act as both a prooxidant and as a scavenger of reactive species such as peroxynitrite. Excessive nitric oxide produced during reperfusion reacts with superoxide to produce the potent reactive species peroxynitrite. Such radicals and reactive oxygen species attack cell membrane lipids, proteins, and glycosaminoglycans, causing further damage. They may also initiate specific biological processes by redox signaling.

Reperfusion can cause hyperkalemia. Reperfusion injury is a primary concern in liver transplantation surgery.

Acute Myeloid Leukemia.

Constitutive activation of Rho kinase (ROCK) is observed in cells bearing oneogenic forms of KIT, FLT3, and BCR-ABL, which is dependent on PI3K and Rho GTPase. Genetic or pharmacologic inhibition of ROCK in oncogene-bearing cells impaired their growth as well as the growth of acute myeloid leukemia patient-derived blasts and prolonged the life span of mice bearing myeloproliferative disease. Downstream from ROCK, rapid dephosphorylation or loss of expression of myosin light chain resulted in enhanced apoptosis, reduced growth, and loss of actin polymerization in oncogene-bearing cells leading to significantly prolonged life span of leukemic mice.

Disease Risk.

The present invention also contemplates treating individuals at risk for any of the aforementioned disease states. These individuals would include those persons suffering from cardiac disease, obesity, diabetes, metabolic syndrome, glaucoma, kidney disease, pulmonary hypertension or arterial hypertension.

B. Combined Therapy

In another embodiment, it is envisioned to use a peptide of the present disclosure in combination with other therapeutic modalities. Thus, in addition to the therapies described above, one may also provide to the patient more "standard" pharmaceutical therapies. Combinations may be achieved by contacting cells, tissues or subjects with a single composition or pharmacological formulation that includes both agents, or by contacting the cell with two distinct compositions or formulations, at the same time, wherein one composition includes the expression construct and the other includes the agent. Alternatively, the therapy using a peptide of the present disclosure may precede or follow administration of the other agent(s) by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell, tissue or subject. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a peptide of the present disclosure, or the other agent will be desired. In this regard, various combinations may be employed. By way of illustration, where the peptide of the present disclosure is "A" and the other agent is "B," the following permutations based on 3 and 4 total administrations are exemplary:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are likewise contemplated. Non-limiting examples of a pharmacological therapeutic agents that may be used in combination with peptides of the present disclosure include a second ROCK1 inhibitor, an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, an antibacterial agent or a combination thereof. Also contemplated for combination with a peptide of the present disclosure are any of the agents/therapies discussed below.

C. Pharmacological Therapeutic Agents

Pharmacological therapeutic agents and methods of administration, dosages, etc., are well known to those of skill in the art (see for example, the "Physicians Desk Reference," Klaassen's "The Pharmacological Basis of Therapeutics," "Remington's Pharmaceutical Sciences," and "The Merck Index, Eleventh Edition," incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art. Moreover, for human administration, preparations should meet sterility, pyrogenicity, general safety and purity standards as required by FDA Office of Biologics standards.

Where clinical applications are contemplated, pharmaceutical compositions will be prepared in a form appropriate for the intended application. Generally, this will entail preparing compositions that are essentially free of pyrogens, as well as other impurities that could be harmful to humans or animals. One will generally desire to employ appropriate salts and buffers to render peptides stable and allow for uptake by target cells. Buffers also will be employed when recombinant cells are introduced into a patient. Aqueous compositions of the present invention comprise an effective amount of the peptides, dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into cardiac tissue. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

For oral administration the peptides of the present disclosure generally may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including gels, pastes, powders and slurries. The active ingredient may be added in a therapeutically effective amount to a paste dentifrice that may include water, binders, abrasives, flavoring agents, foaming agents, and humectants.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure.

IV. KITS

Any of the compositions described herein may be comprised in a kit. In a non-limiting example, a peptide is included in a kit. The kit may further include a sterile buffer to facilitate dilution. The kit may, also include one or more devices for delivery, such as a syringe or catheter.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the active agent may be provided as dried powder(s). When reagents and/or components are provided as a dry powder, the powder can be reconstituted by the addition of a suitable solvent. It is envisioned that the solvent may also be provided in another container means. Such kits may also include components that preserve or maintain the active agent that protect against its degradation.

The kits of the present invention will also typically include a means for containing the vials in close confinement for commercial sale, such as, e.g., injection and/or blow-molded plastic containers into which the desired vials are retained. A kit will also include instructions for employing the kit components as well the use of any other reagent not included in the kit. Instructions may include variations that can be implemented.

It is contemplated that such reagents are embodiments of kits of the invention. Such kits, however, are not limited to the particular items identified above and may include any reagent used for the manipulation or characterization of miRNA.

V. SCREENING METHODS

The present invention further comprises methods for identifying peptide inhibitors of ROCK1 that are useful in the prevention or treatment of the diseases discussed above. These assays may comprise random screening of large libraries of candidate substances; alternatively, the assays may be used to focus on particular classes of compounds selected with an eye towards structural attributes that are believed to make them more likely to inhibit ROCK1, such as those based on structural features found in the peptides of the present disclosure.

To identify a ROCK1 inhibitor, one generally will determine the function of ROCK1 in the presence and absence of the candidate peptide. For example, a method generally comprises:
(a) providing a candidate peptide;
(b) admixing the candidate peptide with ROCK1;
(c) measuring ROCK1 activity; and
(d) comparing the activity in step (c) with the activity in the absence of the candidate peptide.
wherein a reduction in the measured activities in the presence of the candidate peptide indicates that the candidate peptide is, indeed, an inhibitor of ROCK1.
Assays also may be conducted in isolated cells, organs, or in living organisms.

It will, of course, be understood that all the screening methods of the present invention are useful in themselves notwithstanding the fact that effective candidates may not be found. The invention provides methods for screening for such candidates, not solely methods of finding them.

VI. VECTORS FOR CLONING, GENE TRANSFER AND EXPRESSION

Within certain embodiments expression vectors may be employed to express the peptides of the present disclosure. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are well know, as are the conditions for the use of dominant drug selection markers for establishing permanent, stable cell clones expressing the products, as well as elements that links expression of the drug selection markers to expression of the peptide.

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988, Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubinstein, 1988; Temin, 1986). Non-viral methods are also known.

VII. EXAMPLES

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Results

Potential Inhibitors Isolated from Phage-Displayed Peptides.

The ROCK1 catalytic domain (MBP-ROCK1) was linked to a maltose binding protein fusion protein and was incubated with a Ph.D-12 phage display library of 12 amino acids in length (New England Biolabs, Inc.). Under high ATP levels (1 mM) which blocked Y27632 inhibitory activity, the inventors found one peptide PD2w-5 (named peptide25 hereafter) that blocked ROCK autophosphorylation. Sequencing results of that inhibitory polypeptide yielded a peptide: ERTYSPSTAVRS (Pep25-4; SEQ ID NO: 49).

Peptide25 Disrupts the Cellular Cytoskeleton.

Peptides25 was synthesized and an additional synthesis which contained a fusion of the N' end terminal TAT sequence (TATpeptide25), which allows peptides and proteins easy entry into cells. The inventors observed a disassociated or "melted" cellular cytoskeleton, as expected for a ROCK inhibitor. The TAT polypeptide sequence alone was ineffective. At the cellular level, the cell cytoskeleton changed after TATpeptide25 was introduced into cell culture medium as expected, since ROCK is a mediator for cell morphology and cell migration.

Wound Healing.

Peptide25 significantly reduces the ability of cell to move into the wound from a scratch test by inhibiting ROCK1 as measured by the change in perimeter at the intersection of the scratch. Peptide25 change in perimeter (mean: 15%; p-value: 0.03) was evaluated for 4 separate experiments with each having 3 trials for a total of 12 measurements. These experiments included two controls, one with no treatment the other with only the TAT peptide.

The Activation Loop Bound Peptide25.

Highly purified MBP-ROCK1 and was mixed with peptide25 and cross-linking reagent DFDNB (1,5-difluoro-2,4-dinitrobenzene), MBP-ROCK1 plus cross-linked peptide25 was digested with Trypsin and the peptide fragments were detected by mass spectroscopy. From the MALDI-TOF-MS data, among the tryptic peptides pool, a unique peptide with m/z of 1430.1 is present from DFDNB-crosslinked inhibitory peptide25/ROCK kinase complex, which did not exist in the crosslinked ROCK alone sample. This corresponds to a molecule in which peptide25 ERTYSPSTAVRS (Pep25-4; SEQ ID NO: 49) binds to the fragment MNKEGMVR (SEQ ID NO: 74) on ROCK. This localizes the binding epitope near the edge of the active loop of ROCK. Interestingly, the "Activation Loop," which in many kinases is the site of regulatory phosphorylation or interaction with activity modulators, showed considerable structural diversity across the kinase family. This diversity extended from the C-terminal portion of β9 strand to the αEF coil. The most exciting aspect of identifying the activation loop, as a site for targeting drugs, is their virtual specificity for each kinase; thus increasing the chances for generating specific protein kinase inhibitors, with little or no cross inhibitory activity.

NMR Spectroscopy Validates the Role of Tyrosine.

Nuclear Magnetic Resonance spectroscopy was used to probe binding interactions between the ROCK1 kinase catalytic domain and the peptide25. STD-NMR (Saturation Transfer Difference-NMR) was used to observe resonances from peptide atoms that are in contact with ROCK. TOCSY and ROESY NMR experiments on the free peptide were also collected and assigned using backbone ROE transfer information. Interestingly, the signal from tyrosine4 on the peptide remained unattenuated, indicative of its role in the peptide-binding interface.

Figure 5:
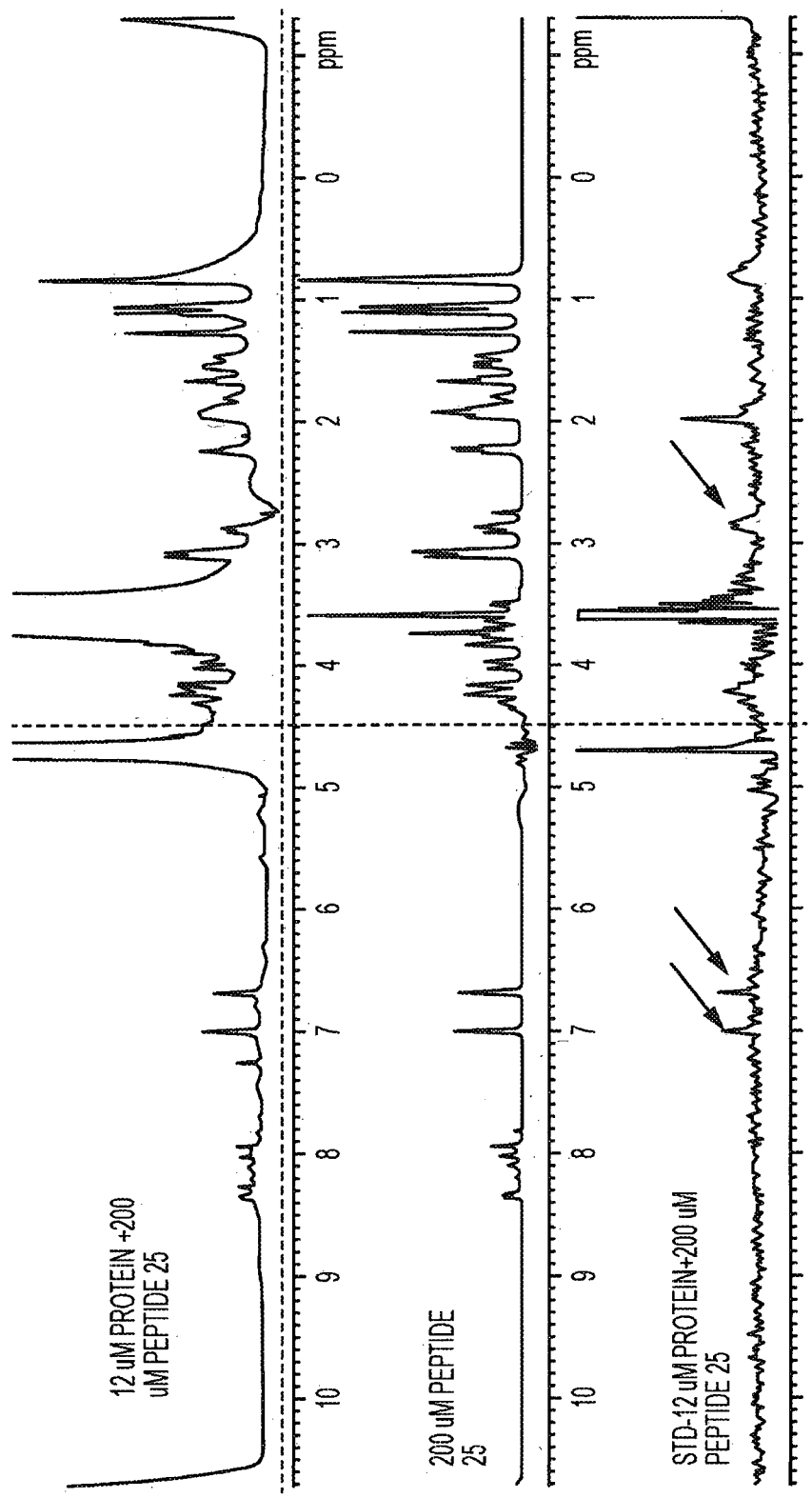
FIG. 5—Saturation Transfer Difference (STD)-NMR shows interaction with Tyr. Top row is from peptide25 and ROCK1 complex, and the middle row is ROCK1 alone using conventional NMR. The lower row is from STD-NMR, which identifies the interaction between ROCK1 and the Tyr of peptide25.
Figure 6:
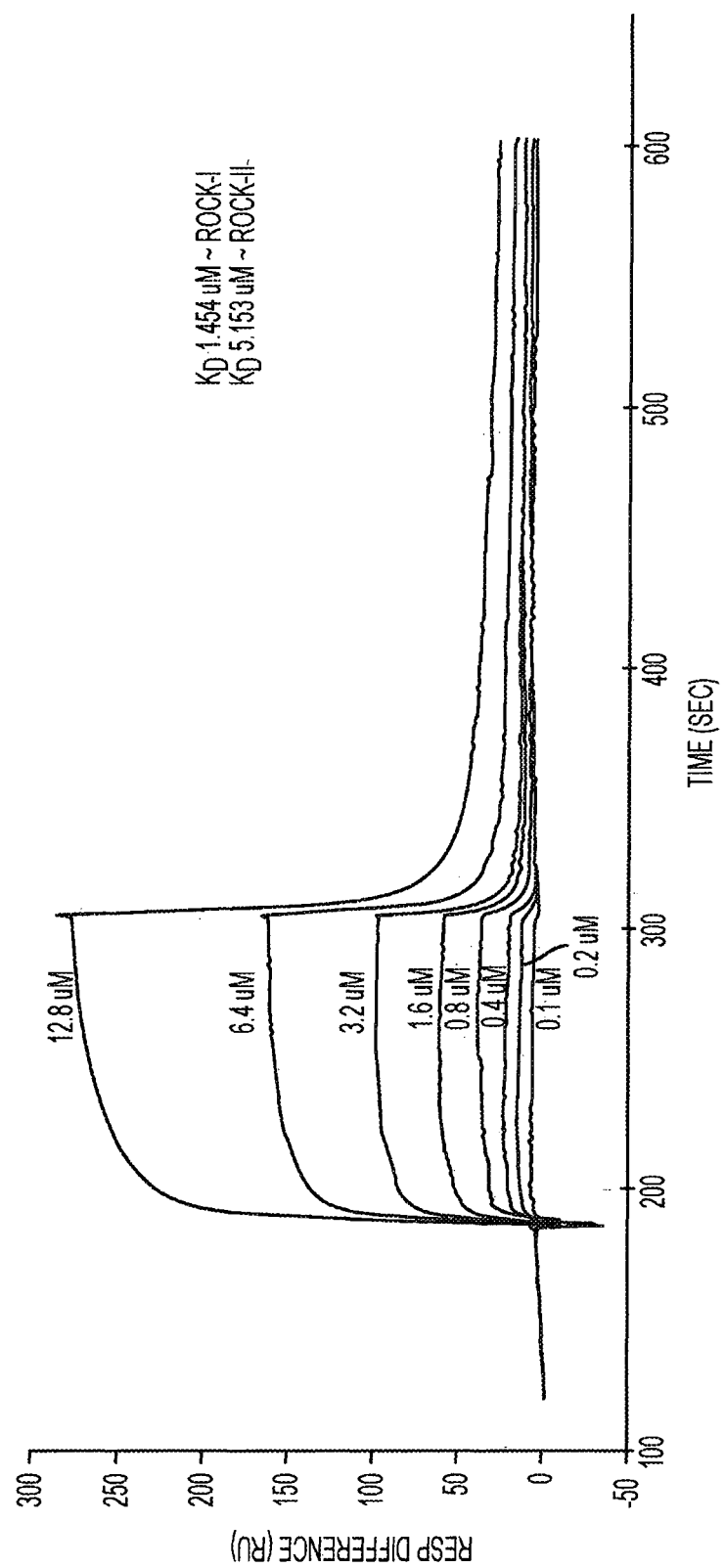
FIG. 6—Determination of binding affinity of TATpeptide25. Proteins MBP, ROCK2, ROCK1-553. ROCK1-415 Were immobilized on CM-5 chip and peptide binding affinity was monitored by BiaCore system. Peptide TAT was used as control to monitored non-specific binding.

Saturation transfer difference (STD)-NMR experiment was used to determine the binding epitopes of the ligands. The STD-NMR method, developed by the Keck/IMD NMR Center at the University of Houston, was applied to the mixture of small molecule of peptide25 and protein ROCK. Data was collected from the samples of ROCK only, peptide25 only, and ROCK/peptide25 complex. The specta demonstrate that an interaction exists between ROCK and peptide25. The STD spectrum (FIG. 5, bottom), displays resonances at 6.8 and 7.0 ppm from peptide25 Tyr Hε and Hδ and 2.85-2.9 ppm from Tyr Hβ. Resonances are, also present from peptide25 Val Hβ (2.0 ppm) and Hγ (0.8 ppm). These results indicate that peptide25 (ERTYSPSTAVRS; SEQ ID NO: 49), makes contacts with ROCK that include the unique Tyr and Val residues.

Surface Plasmon Resonance.

Surface Plasmon Resonance (SPR) was used to measure peptide25 binding efficiency with ROCK. The binding affinity of ROCK1 and peptide25 was established as 1.5 uM. The binding of peptide25 with ROCK1 as compared to ROCK2 (data not shown) demonstrated some difference even though both proteins have 95% similarity in sequence in the kinase domain. Interestingly, ROCK1 and ROCK2 have a sequence variation in the activation loop, which might explain the higher affinity of peptide25 to ROCK1.

Critical Residues of Peptide25.

Figure 8:
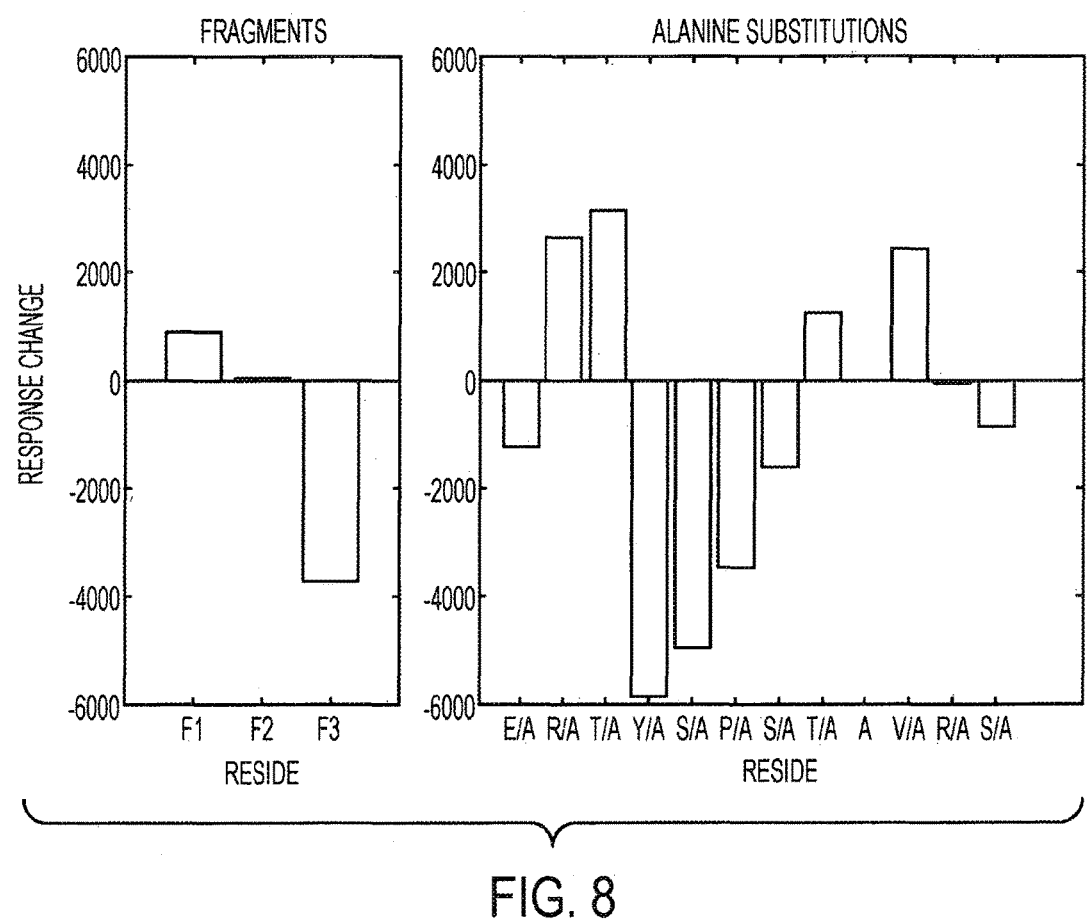
FIG. 8—(Left panel) Fragments F1: ERTYS (SEQ ID NO: 3), F2: YSPST (SEQ ID NO: 4), F3: STAVRS (SEQ ID NO: 2) showed that F1 and F2 retained its activity as measured by a luciferase assay; while F3 did not confer an inhibitory response. (Right panel) Likewise the alanine substitution at positions Y4, S5, P6, and S7 all reduced the effectiveness of peptide25.

The peptide25 was divided into fragments; ERTYS (F1; SEQ ID NO: 3), YSPST (F2; SEQ ID NO: 4), and STAVRS (F3; SEQ ID NO: 2). The first two fragments retained activity while the last fragment lost effectively (FIG. 8). Additionally, an alanine substitution was performed at each position to look for amino acids that putatively might be important to binding and when replaced reduced the response. Amino acids $Y_4$, $S_5$, $P_6$, and $S_7$ all showed reduction in binding response when substituted with an alanine (FIG. 8) and were selected for inclusion in candidates for testing shorter peptides.

Peptide25 Fragments Biological Activity Evaluation.

Figure 9:
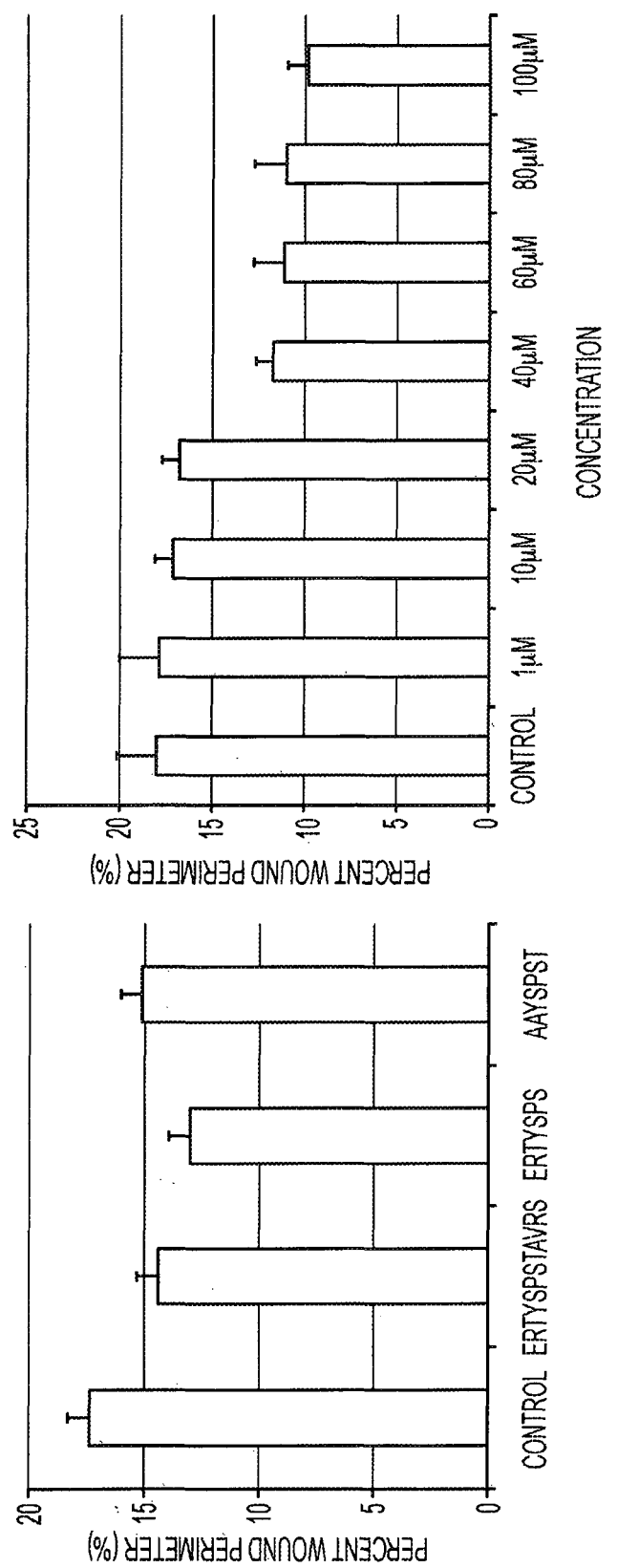
FIG. 9—(Left panel) The percent of healing measured from a standard scratch test indicated that ERTYSPS (SEQ ID NO: 69) was more, significant (mean: 13.1; p value: 0.004) as compared to AAYSPST (SEQ ID NO: 62) (mean: 15.1; p value 0.03) but both demonstrated inhibition as compared to the control (mean: 17.4) in an experiment with at least N=5 trials. (Right panel) Dose curve for peptide ERTYSPS (SEQ ID NO: 69) indicates that 40 µM was the effective dose.

Peptide fragments were chosen based on the information from analysis of critical residues and the candidate sequences Pep25-A AAYSPST (Pep25-A; SEQ ID NO: 62) and ERTYSPS (Pep25-P2; SEQ ID NO: 69) were evaluated again using a wound healing scratch test. The alanine substitution data indicated that a R2A and T3A substitution might improve inhibition (FIG. 9). However, analysis of the candidate peptide AAYSPST (Pep25-A; SEQ ID NO: 62) compared to the fragment ERTYSPS (Pep25-P2; SEQ ID NO: 69) demonstrated that ERTYSPS (Pep25-P2; SEQ ID NO: 69) inhibited ROCK1 more effectively (FIG. 9), Evaluation of ERTYSPS (Pep25-P2; SEQ ID NO: 69) dose response identified 40 μM as a useful dose.

Pep25-P2 Identified as "Best" Peptide.

Figure 10:
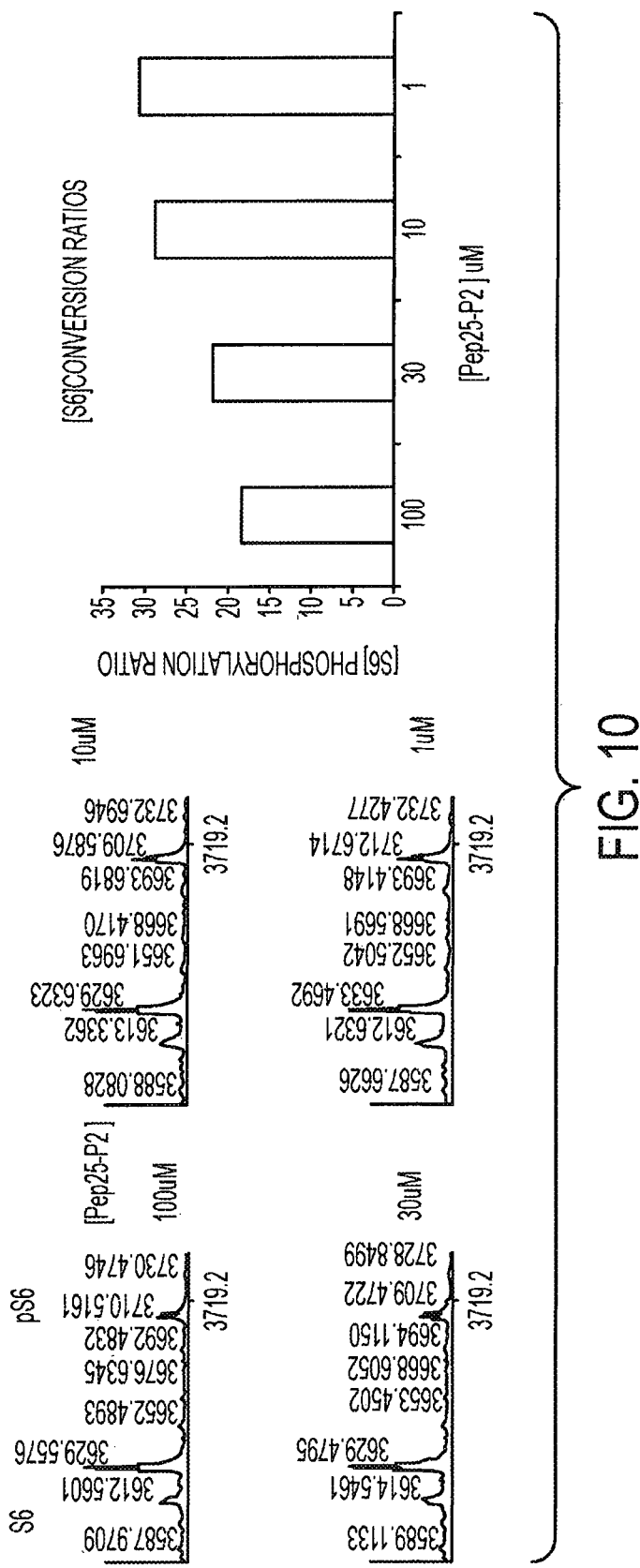
FIG. 10—(Left panel) Mass spectrum, two peaks labeled as S6 and pS6 were non-phosphorylated and phosphorylated S6 from ROCK reaction mixture. Following the decreasing concentration of Pep25-P2, the phosphorylated peak pS6 was increasing. (Right panel) S6 conversion ratios were calculated by phosphorylated peak area divided by the sum of phosphorylated and non-phosphorylated peaks' areas.

From different biological activity evaluations, Pep25-P2 was identified as the most effective peptide inhibitor from the pool of pep25 derivatives. Mass spectrum data showed Pep25-P2 couldn't be phosphorylated by ROCK. To determine its inhibition at substrate conversion, different concentrations of Pep25-P2 was added to a ROCK and S6 (substrate) reaction mixture. In MS data, peaks representing phosphorylated and non-phosphorylated S6 substrates were then identified (FIG. 10). The Conversion Ratios of the phosphorylated peak area to the sum of phosphorylated peak and non-phosphorylated peaks' areas led to the observation that Pep25-P2 repressed the phosphorylation of substrate S6 by ROCK.

Ring Bath Experiment.

Figure 11:
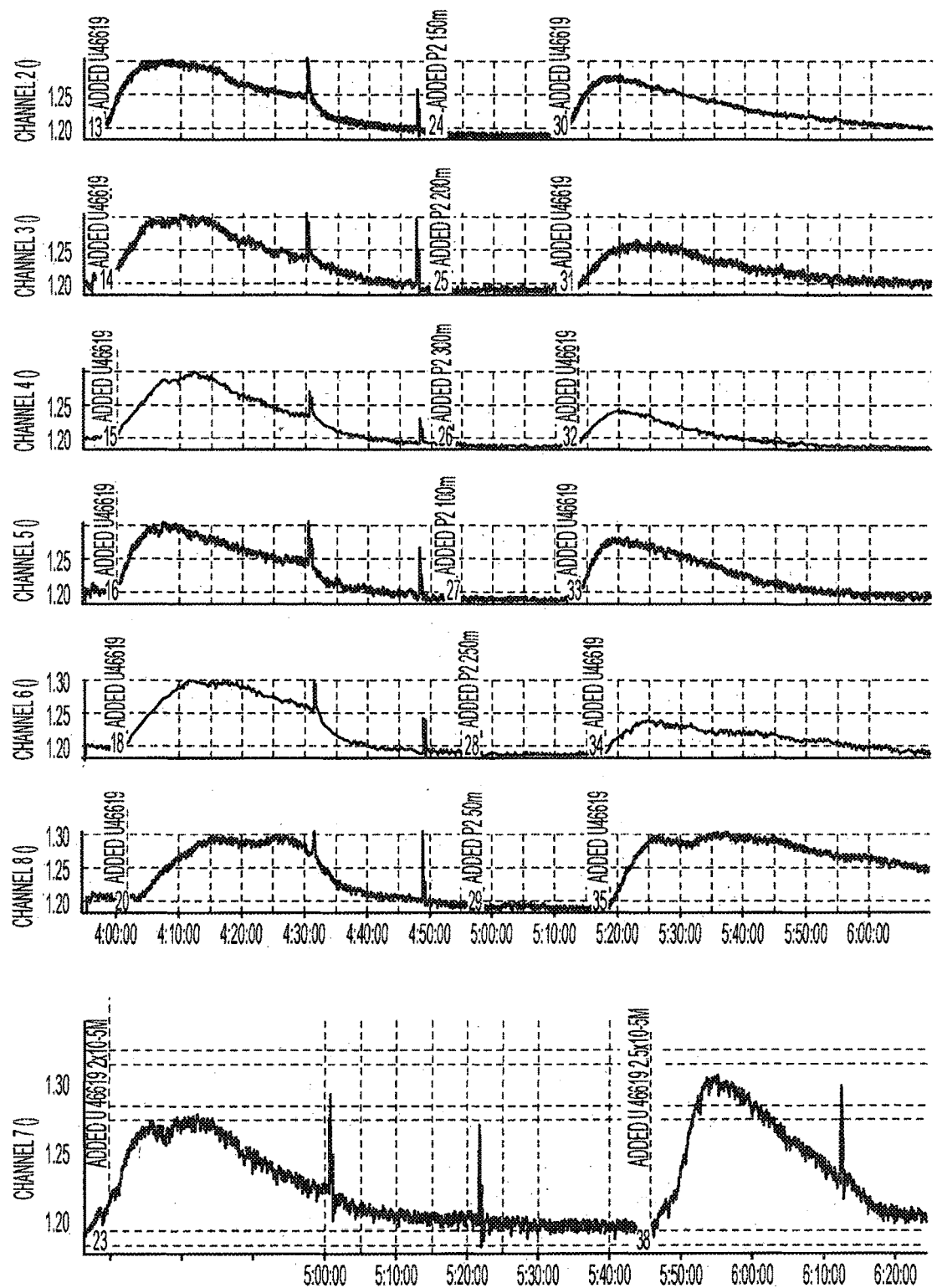
FIG. 11—The dose dependant response curves of the aortic ring contractility assay in which the first injection is the sensitation using the vasoconstrictor U46619 followed by a preincubation of Pep25-P2 for 20 min and evaluated by a second injection of U46619. Channel evaluation of concentrations 150, 200, 300, 100, 250, and 50 µM. Channel 7 (last graph) is the control.
Figure 12:
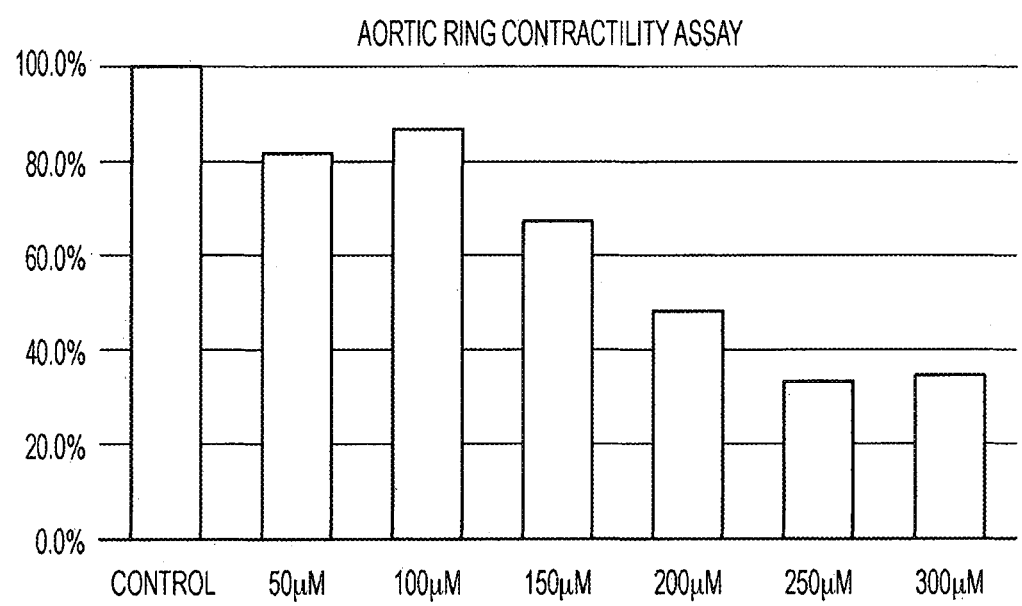
FIG. 12—Aortic ring contractility assay summary for each concentration and the control demonstrates a dose dependant response and effectiveness of Pep25-P2 up to 300 µM.

Aortas were collected from adult mice, removed the surrounding fat tissues and installed the freshly cut rings in 2 mm sections on the isometric transducer apparatus. After adjusting the rings tension through series of contraction and relaxation, the rings were constricted 3 times with the 40 mM KCl to achieve consistent contraction. In order to find the effective contraction inducing dose of U46619, following the relaxation of the rings after the KCl contraction, the rings were subjected to contraction by adding different doses of U46619, a vasoconstrictor. 1-3 nM U46619 was chosen do the further experiments. The rings were contracted by adding the U46619 compound and following the completion of isometric contraction, different doses of Pep25-P2 (200 and 300 μM) were preincubated with the rings for 10 min. Second dose of U46619 was applied to contract the ring. The affection was measured by the difference of the highest response of U46619 with and without Pep25-P2. Experimental results showed that the peptide P2 showed suppression of contractility of U46619. One ring had 26% decreasing, the other had 40% decreasing. In FIGS. 11-12, the dose dependant response curves of the aortic ring contractility assay in which the first injection is the sensitation using the vasoconstrictor U46619 followed by a preincubation of Pep25-P2 for 20 min and evaluated by a second injection of U46619. Aortic ring contractility assay summary for each concentration and the control demonstrates a dose dependant response and effectiveness of Pep25-P2 up to 300 μM.

Example 2—Discussion

A common problem for development of any protein kinase inhibitor is to find an antagonist highly specific to an individual kinase. Since the catalytic pocket of virtually all kinases have the same highly conserved sequences such as the critical ATP binding residue at the alpha-helix and catalytic residues at the N-helix, many widely used kinase inhibitors are actually ATP-competitors (Nolen et al., 2004). In fact ROCK inhibitors Y27632 and Fusadil also inhibit protein kinase A, protein kinase C and citron kinase. One of the most often discussed dynamic motions of the protein kinase core is the opening and closing of the catalytic cleft through rotation of the lobes (Nolen et al., 2004). Evidence is accumulating that this rotation is a normal part of the catalytic cycle and is a requirement for kinase activity. The inventors sought to find inhibitors that have allosteric binding characteristics that might provide for kinase specificity. This was motivated by the observation that many current kinase inhibitors are in fact ATP competitors. Their strategy was to search for inhibitors using a phage display library and evaluate activity in a fluorescent assay. Thus, the approach was to identify short polypeptides that may interfere with ROCK1 activity by altering conformational changes during the catalytic cycle.

The inventors discovered a powerful inhibitory polypeptide through repetitive panning of an M13 phage display library, with a ROCK1 catalytic domain-maltose binding fusion protein. Some of those peptides had sequences which were possible substrates and culled from the inventors' candidate list, while two peptides PD2w-5 and PD3w-5 exhibited autophosphorylated inhibition. PD3w-3 (peptide25) became an initial lead based on its binding response and localization of binding on the activation loop of the ROCK1 catalytic domain. Peptide25 blocked ROCK1 activity in the presence of mM ATP. Mapping of the peptide25 binding epitope of ROCK1 using DFDNB cross-linking reaction revealed linkage to the "Activation Loop", an accessible but poorly conserved sequence not shared with other protein kinases; thus, indicating a novel locus to direct a new class of inhibitory drugs. Localization of its binding epitope on the activation loop encouraged the inventors' team because of the activation loop of kinases is both important to catalytic function regulation and has significant diversity across the kinase family. This diversity in activation loop sequence might confer specificity to a lead compound to ROCK1, enhancing its viability for further study. The inventors optimized ROCK1 inhibitory peptides through synthesis of alanine scanning mutants and truncation mutants of peptide25 to determine the fewest number of amino acids still critical for binding to the ROCK1 activation loop. Alanine substitutions for amino acids in the peptide were evaluated and a region on the N-terminus of the peptide was found to contribute to the peptides binding response to ROCK1. STD-NMR experiments confirmed the direct contact through the identifiable chemical shifts of the peptide25 tyrosine with the protein. Further more, surface plasmon resonance data found that peptide25 bad a Kd of 1.5 μM.

Using this information, the inventors tested the fragment ERTYSPS (Pep25-P2; SEQ ID NO: 69) among many other candidate fragments or amino a substitutions. Computation docking of peptide candidates further strengthened the hypothesis that binding could occur along the N-lobe/C-lobe grove toward the activation loop. Activity of the candidate ERTYSPS (SEQ ID NO: 69 Pep2S-P2) was measured in a fluorescence assay, and it inhibited wound healing and disrupted actin exoskeleton formation like the inventors' original peptide25. These data together indicate that an important allosteric binding mode in the N-lobe/C-lobe grove toward the activation loop inhibits the activity of ROCK1. These data provide a new prospective in the regulation of ROCK1.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. REFERENCES

The following references, to the extent that they provide exemplary procedural or other details supplementary to those set forth herein, are specifically incorporated herein by reference.

Amano et al., *Journal of Biological Chemistry*, 274(45): p. 32418-32424, 1999.
Baichwal and Sugden. In: Gene Transfer, Kucherlapati (Ed.), Plenum Press, NY. 117-148, 1986.
Bodanszky et al., *J. Antibiot.*, 29(5):549-53, 1976.
Bristow, *Cardiology*, 92:3-6, 1999.
Chang. *Proc Natl Acad Sci USA*, 103(39):14495-500, 2006.
Chen et al., *Journal of Biological Chemistry*, 277(15): p. 12680-12688, 2002.
Duong-Quy et al., *Pharmacol Ther.*, 137(3):352-64, 2013
Durand et al., *Ann. Med.*, 27:311-317, 1995.
Dvorsky et al., *Journal of Biological Chemistry*, 279(8): p. 7098-7104, 2004.
Fischer, *Med. Res. Rev.*, 27(6):755-796, 2007.
Haudek et al., Cardiovascular Research, 83(3): p. 511-518, 2009.
Ishizaki et al., *EMBO J* 15(8): p. 1885-1893, 1996.
Jacobs et al., *Journal of Biological Chemistry* 281(1): p. 260-268, 2006.
Merrifield, *J. Am. Chem. Soc.*, 85(14):2149-2154, 1963.
Narula et al., *Cardiology Clinics* 19(1): p. 113-126, 2001.
Nicolas and Rubinstein. In: Vectors: A survey of molecular cloning vectors and their uses, Rodriguez and Denhardt (Eds), Stoneham: Butterworth. 494-513, 1988.
Nolen et al. *Molecular Cell* 15(5): p. 661-675, 2004.
Peptide Synthesis, 1985
Protective Groups in Organic Chemistry, 1973
Ridgeway, In: Vectors: A Survey of Molecular Cloning Vectors and Their Uses, Rodriguez et al. (Eds.), Stoneham: Butterworth, 467-492, 1988.
Schafmeister et al., *J. Amer. Chem. Soc.*, 122(24):5891-5892, 2000.
Shimizu et al., *Journal of Biological Chemistry* 278(46): p. 46046-46051, 2003.
Solid Phase Peptide Synthelia, 1984
Temin, In: Gene Transfer, Kucherlapati (Ed.), NY, Plenum Press, 149-188, 1986.
T Ishizaki et al., *EMBO J.*, 15(8): p. 1885-1893, 1996.
U.S. Pat. No. 5,604,251
U.S. Pat. No. 5,889,155
U.S. Pat. No. 6,261,569
U.S. Pat. No. 7,183,059
U.S. Pat. No. 7,192,713
Wei et. al., *Development* 129(7): p. 1705-1714, 2002.
Wei et al., *FASEB J.* 18(7): p. 857-859, 2004.
WO 98/33791
Yamaguchi et al., *Structure* 14(3): p. 589-600, 2006.
Zhang et al., *FASEB J* 20(7): p. 916-925, 2006.

What is claimed is:

1. A method of treating cardiovascular disease and/or conditions involving remodeling comprising administering to a subject in need thereof a pharmaceutical composition comprising (a) a peptide consisting of 4-30 residues and exhibiting the sequence ERTYSPS (SEQ ID NO: 69) and (b) a pharmaceutically acceptable buffer, excipient or diluent.

2. The method of claim 1, wherein the peptide consists of 5, 6, 7, 8, 9, 10, 11, 12, 13, 14, 15, 16, 17, 18, 19, 20, 21, 22, 23, 24, 25 or 30 residues.

3. The method of claim 1, wherein the peptide consists of the sequence ERTYSPS (SEQ ID NO: 69).

4. The method of claim 1, wherein the peptide comprises the sequence ERTYSPSTAVRS (SEQ ID NO: 49).

5. The method of claim 1, wherein the peptide consisting of the sequence ERTYSPSTAVRS (SEQ ID NO: 49).

6. The method of claim 1, wherein the peptide further comprises one or more D-amino acid residues.

7. The method of claim 1, wherein the peptide further comprises all D-amino acid residues.

8. The method of claim 1, wherein administering the inhibitor is performed intramuscularly, intravenously or by direct injection into cardiac tissue.

9. The method of claim 1, wherein administering the inhibitor comprises oral, transdermal, sustained release, controlled release, delayed release, suppository, or sublingual administration.

10. The method of claim 1, further comprising administering said peptide to said subject at least a second time.

11. The method of claim 10, wherein said peptide is administered chronically to said subject.

12. The method of claim 1, further comprising administering to said patient a second heart disease therapy.

13. The method of claim 12, wherein said second therapy is selected from the group consisting of a second ROCK inhibitor, a beta blocker, an ionotrope, a diuretic, ACE-I, AII antagonist, BNP, or a $Ca^{++}$ channel blocker.

14. The method of claim 1, wherein treating comprises improving one or more symptoms of heart failure.

15. The method of claim 14, wherein said one or more improved symptoms comprises increased exercise capacity, increased cardiac ejection volume, increased cardiac ejection fraction, decreased left ventricular end diastolic pressure, decreased pulmonary capillary wedge pressure, increased cardiac output, or cardiac index, lowered pulmonary artery pressures, decreased left ventricular end systolic and diastolic dimensions, decreased left and right ventricular wall stress, decreased wall tension, increased quality of life, and decreased disease-related morbidity or mortality.

* * * * *